United States Patent
Lennon et al.

[11] Patent Number: 5,939,252
[45] Date of Patent: Aug. 17, 1999

[54] DETACHABLE-ELEMENT ASSAY DEVICE

[76] Inventors: Donald J. Lennon, 12 Applecrest Dr., Yarmouth, Me. 04096; Roger N. Piasio, 233 Foreside Rd., Cumberland, Me. 04110

[21] Appl. No.: 08/853,760

[22] Filed: May 9, 1997

[51] Int. Cl.⁶ .......................... C12Q 1/00; G01N 33/543
[52] U.S. Cl. .................. 435/4; 422/58; 435/4; 435/7.1; 435/7.2; 435/7.92; 435/7.93; 435/7.94; 435/7.95; 435/970; 435/975; 435/7.32; 435/7.34; 436/518; 436/525; 436/807; 436/808; 436/825
[58] Field of Search .................. 422/58; 435/4, 435/7.1, 7.2, 970, 975, 7.92–7.95, 7.32, 7.33, 7.34; 436/518, 525, 807, 809, 825

[56] References Cited

U.S. PATENT DOCUMENTS

| | | |
|---|---|---|
| 30,267 | 5/1860 | Bruschi . |
| 31,006 | 8/1861 | Schuurs et al. . |
| 35,306 | 7/1862 | Chen et al. . |
| 3,511,608 | 5/1970 | Anderson . |
| 3,620,677 | 11/1971 | Morison . |

(List continued on next page.)

FOREIGN PATENT DOCUMENTS

| | | |
|---|---|---|
| 0063810 | 11/1982 | European Pat. Off. . |
| 0093595 | 11/1983 | European Pat. Off. . |
| 0125118 | 11/1984 | European Pat. Off. . |
| 0154749 | 9/1985 | European Pat. Off. . |
| 0170746 | 2/1986 | European Pat. Off. . |
| 0183442 | 6/1986 | European Pat. Off. . |
| 0204579 | 12/1986 | European Pat. Off. . |
| 0217403 | 4/1987 | European Pat. Off. . |
| 0225054 | 6/1987 | European Pat. Off. . |
| 0227173 | 7/1987 | European Pat. Off. . |
| 0238012 | 9/1987 | European Pat. Off. . |
| 0250137 | 12/1987 | European Pat. Off. . |
| 0253579 | 1/1988 | European Pat. Off. . |
| 0262328 | 4/1988 | European Pat. Off. . |
| 0267724 | 5/1988 | European Pat. Off. . |
| 0269876 | 6/1988 | European Pat. Off. . |
| 0279097 | 8/1988 | European Pat. Off. . |
| 0279574 | 8/1988 | European Pat. Off. . |
| 0281251 | 9/1988 | European Pat. Off. . |
| 0284232 | 9/1988 | European Pat. Off. . |
| 0286371 | 10/1988 | European Pat. Off. . |
| 0291194 | 11/1988 | European Pat. Off. . |
| 0296724 | 12/1988 | European Pat. Off. . |
| 0297292 | 1/1989 | European Pat. Off. . |
| 0299428 | 1/1989 | European Pat. Off. . |
| 0306772 | 3/1989 | European Pat. Off. . |
| 0317001 | 5/1989 | European Pat. Off. . |
| 0322340 | 6/1989 | European Pat. Off. . |
| 0323605 | 7/1989 | European Pat. Off. . |
| 0383619 | 8/1990 | European Pat. Off. . |
| 0415679 | 3/1991 | European Pat. Off. . |
| 0420021 | 4/1991 | European Pat. Off. . |
| 0443231 | 8/1991 | European Pat. Off. . |

(List continued on next page.)

*Primary Examiner*—Carol A. Spiegel
*Attorney, Agent, or Firm*—William H. May; P. R. Harder; Merchant & Gould

[57] ABSTRACT

An assay device for detection or determination of an analyte in a sample uses either removably attachable components or hinged panels to provide greater flexibility and reduce manufacturing and storage costs. In one embodiment of the device, the device comprises: (1) a first opposable component including:(a) a first panel; (b) a second panel mounted on the first panel generally parallel to the first panel with space between the first and second panel, the second panel having an opening forming a first receptacle for a sample collection device; and (c) a second receptacle for a test strip formed by the first panel and the second panel; and (2) a second opposable component hingedly attached to the first opposable component. In this device, the first and second opposable components can be brought into operable contact so that fluid is expressed from the sample collection device and applied to the test strip for detection or determination of an analyte by a test performed on the test strip. Other embodiments of devices are included, as well as test kits and method of use of the devices.

85 Claims, 4 Drawing Sheets

U.S. PATENT DOCUMENTS

| | | |
|---|---|---|
| 3,644,177 | 2/1972 | Zyk . |
| 3,720,760 | 3/1973 | Bennich et al. . |
| 3,723,064 | 3/1973 | Liotta . |
| 3,785,930 | 1/1974 | Ellis . |
| 3,798,004 | 3/1974 | Zerachia et al. . |
| 3,888,629 | 6/1975 | Bagshawe . |
| 3,893,808 | 7/1975 | Campbell . |
| 3,901,657 | 8/1975 | Lightfoot . |
| 3,915,647 | 10/1975 | Wright . |
| 3,933,594 | 1/1976 | Milligan et al. . |
| 3,990,850 | 11/1976 | Friedman et al. . |
| 3,992,158 | 11/1976 | Przybylowicz et al. . |
| 4,012,198 | 3/1977 | Finter et al. . |
| 4,018,662 | 4/1977 | Ruhenstroth-Bauer et al. . |
| 4,042,335 | 8/1977 | Clement . |
| 4,055,394 | 10/1977 | Friedman et al. . |
| 4,066,403 | 1/1978 | Bruschi . |
| 4,094,647 | 6/1978 | Deutsch et al. . |
| 4,108,729 | 8/1978 | Mennen . |
| 4,110,079 | 8/1978 | Schaeffer et al. . |
| 4,144,306 | 3/1979 | Figueras . |
| 4,153,668 | 5/1979 | Hill et al. . |
| 4,160,008 | 7/1979 | Fenocketti . |
| 4,168,146 | 9/1979 | Grubb et al. . |
| 4,189,304 | 2/1980 | Adams, Jr. . |
| 4,200,690 | 4/1980 | Root et al. . |
| 4,212,742 | 7/1980 | Solomon et al. . |
| 4,225,557 | 9/1980 | Hartl et al. . |
| 4,233,029 | 11/1980 | Columbus et al. . |
| 4,235,601 | 11/1980 | Deutsch et al. . |
| 4,246,339 | 1/1981 | Cole et al. . |
| 4,248,829 | 2/1981 | Kitajima et al. . |
| 4,254,083 | 3/1981 | Columbus . |
| 4,255,384 | 3/1981 | Kitajima et al. . |
| 4,256,693 | 3/1981 | Kondo et al. . |
| 4,258,001 | 3/1981 | Pierce et al. . |
| 4,271,119 | 6/1981 | Columbus . |
| 4,288,228 | 9/1981 | Oberhardt . |
| 4,301,139 | 11/1981 | Feingers et al. . |
| 4,313,734 | 2/1982 | Leuvering . |
| 4,323,536 | 4/1982 | Columbus . |
| 4,337,065 | 6/1982 | Hiratsuka et al. . |
| 4,361,537 | 11/1982 | Deutsch et al. . |
| 4,363,874 | 12/1982 | Greenquist . |
| 4,365,970 | 12/1982 | Lawrence et al. . |
| 4,366,241 | 12/1982 | Tom et al. . |
| 4,376,110 | 3/1983 | David et al. . |
| 4,390,343 | 6/1983 | Walter . |
| 4,391,904 | 7/1983 | Litman et al. . |
| 4,407,943 | 10/1983 | Cole et al. . |
| 4,425,438 | 1/1984 | Bauman et al. . |
| 4,426,451 | 1/1984 | Columbus . |
| 4,427,769 | 1/1984 | Adlercreutz . |
| 4,435,504 | 3/1984 | Zuk et al. . |
| 4,442,204 | 4/1984 | Greenquist et al. . |
| 4,446,232 | 5/1984 | Liotta et al. . |
| 4,447,526 | 5/1984 | Rupchock et al. . |
| 4,447,546 | 5/1984 | Hirschfeld . |
| 4,459,358 | 7/1984 | Berke . |
| 4,472,498 | 9/1984 | Masuda et al. . |
| 4,474,878 | 10/1984 | Halbert et al. . |
| 4,477,575 | 10/1984 | Vogel et al. . |
| 4,486,530 | 12/1984 | David et al. . |
| 4,486,536 | 12/1984 | Baker et al. . |
| 4,515,889 | 5/1985 | Klose et al. . |
| 4,517,288 | 5/1985 | Giegel et al. . |
| 4,578,358 | 3/1986 | Oksman et al. . |
| 4,582,811 | 4/1986 | Pucci et al. . |
| 4,587,102 | 5/1986 | Nagatomo et al. . |
| 4,594,327 | 6/1986 | Zuk et al. . |
| 4,613,567 | 9/1986 | Yasoshima et al. . |
| 4,615,983 | 10/1986 | Koyama . |
| 4,623,461 | 11/1986 | Hossom et al. . |
| 4,624,929 | 11/1986 | Ullman . |
| 4,631,174 | 12/1986 | Kondo . |
| 4,632,901 | 12/1986 | Valkirs et al. . |
| 4,637,978 | 1/1987 | Dappen . |
| 4,642,285 | 2/1987 | Halbert et al. . |
| 4,645,743 | 2/1987 | Baker et al. . |
| 4,668,619 | 5/1987 | Greenquist et al. . |
| 4,670,381 | 6/1987 | Frickey et al. . |
| 4,676,950 | 6/1987 | Foster . |
| 4,678,757 | 7/1987 | Rapkin et al. . |
| 4,683,197 | 7/1987 | Gallati . |
| 4,690,907 | 9/1987 | Hibino et al. . |
| 4,693,834 | 9/1987 | Hossom . |
| 4,703,017 | 10/1987 | Campbell et al. . |
| 4,717,656 | 1/1988 | Swanljung . |
| 4,727,019 | 2/1988 | Valkirs et al. . |
| 4,738,823 | 4/1988 | Engelmann . |
| 4,740,468 | 4/1988 | Weng et al. . |
| 4,742,002 | 5/1988 | Guadagno . |
| 4,743,560 | 5/1988 | Campbell et al. . |
| 4,752,562 | 6/1988 | Sheiman et al. . |
| 4,753,776 | 6/1988 | Hillman et al. . |
| 4,756,828 | 7/1988 | Litman et al. . |
| 4,757,004 | 7/1988 | Houts et al. . |
| 4,761,381 | 8/1988 | Blatt et al. . |
| 4,770,853 | 9/1988 | Bernstein . |
| 4,775,636 | 10/1988 | Moeremans et al. . |
| 4,780,280 | 10/1988 | Berger et al. . |
| 4,786,594 | 11/1988 | Khanna et al. . |
| 4,789,526 | 12/1988 | Matkovich . |
| 4,789,629 | 12/1988 | Baker et al. . |
| 4,790,979 | 12/1988 | Terminiello et al. . |
| 4,797,260 | 1/1989 | Parker . |
| 4,804,518 | 2/1989 | Levine et al. . |
| 4,806,311 | 2/1989 | Greenquist . |
| 4,806,312 | 2/1989 | Greenquist . |
| 4,810,470 | 3/1989 | Burkhardt et al. . |
| 4,812,293 | 3/1989 | McLaurin et al. . |
| 4,816,224 | 3/1989 | Vogel et al. . |
| 4,818,677 | 4/1989 | Hay-Kaufman et al. . |
| 4,826,759 | 5/1989 | Guire et al. . |
| 4,837,145 | 6/1989 | Liotta . |
| 4,837,373 | 6/1989 | Gunket et al. . |
| 4,839,297 | 6/1989 | Freitag et al. . |
| 4,847,199 | 7/1989 | Snyder et al. . |
| 4,853,335 | 8/1989 | Olsen et al. . |
| 4,855,240 | 8/1989 | Rosenstein . |
| 4,857,453 | 8/1989 | Ullman et al. . |
| 4,859,612 | 8/1989 | Cole et al. . |
| 4,861,711 | 8/1989 | Friesen et al. . |
| 4,868,108 | 9/1989 | Bahar et al. . |
| 4,870,005 | 9/1989 | Akiyoshi et al. . |
| 4,876,067 | 10/1989 | Deneke et al. . |
| 4,877,586 | 10/1989 | Devaney, Jr. et al. . |
| 4,879,215 | 11/1989 | Weng et al. . |
| 4,883,764 | 11/1989 | Kloepfer . |
| 4,895,809 | 1/1990 | Schlabach . |
| 4,900,663 | 2/1990 | Wie et al. . |
| 4,902,629 | 2/1990 | Meserol et al. . |
| 4,912,034 | 3/1990 | Kalra et al. . |
| 4,916,056 | 4/1990 | Brown, III et al. . |
| 4,916,078 | 4/1990 | Klose et al. . |
| 4,918,025 | 4/1990 | Grenner . |
| 4,920,045 | 4/1990 | Okuda et al. . |
| 4,920,046 | 4/1990 | McFarland et al. . |
| 4,931,385 | 6/1990 | Block et al. . |
| 4,933,092 | 6/1990 | Aunet et al. . |
| 4,938,927 | 7/1990 | Kelton et al. . |
| 4,939,098 | 7/1990 | Suzuki et al. . |

| | | |
|---|---|---|
| 4,943,522 | 7/1990 | Eisinger et al. . |
| 4,945,205 | 7/1990 | Litman et al. . |
| 4,952,517 | 8/1990 | Bahar . |
| 4,956,275 | 9/1990 | Zuk et al. . |
| 4,956,302 | 9/1990 | Gordon et al. . |
| 4,959,305 | 9/1990 | Woodrum . |
| 4,959,307 | 9/1990 | Olson . |
| 4,959,324 | 9/1990 | Ramel et al. . |
| 4,960,691 | 10/1990 | Gordon et al. . |
| 4,963,325 | 10/1990 | Lennon et al. . |
| 4,963,468 | 10/1990 | Olson . |
| 4,965,047 | 10/1990 | Hammond . |
| 4,973,549 | 11/1990 | Khanna et al. . |
| 4,976,926 | 12/1990 | Matkovich . |
| 4,977,078 | 12/1990 | Niimura et al. . |
| 4,981,786 | 1/1991 | Dafforn et al. . |
| 4,988,627 | 1/1991 | Smith-Lewis . |
| 4,999,285 | 3/1991 | Stiso . |
| 4,999,287 | 3/1991 | Allen et al. . |
| 5,006,464 | 4/1991 | Chu et al. . |
| 5,006,474 | 4/1991 | Horstman et al. . |
| 5,009,996 | 4/1991 | Shah et al. . |
| 5,009,997 | 4/1991 | Shah et al. . |
| 5,013,669 | 5/1991 | Peters, Jr. et al. . |
| 5,028,535 | 7/1991 | Buechler et al. . |
| 5,030,555 | 7/1991 | Clemmons . |
| 5,030,558 | 7/1991 | Litman et al. . |
| 5,039,607 | 8/1991 | Skold et al. . |
| 5,051,237 | 9/1991 | Grenner . |
| 5,055,195 | 10/1991 | Trasch et al. . |
| 5,064,541 | 11/1991 | Jeng et al. . |
| 5,064,766 | 11/1991 | Wardlaw et al. . |
| 5,071,746 | 12/1991 | Wilk et al. . |
| 5,073,484 | 12/1991 | Swanson et al. . |
| 5,075,078 | 12/1991 | Osikowicz et al. . |
| 5,076,925 | 12/1991 | Roesink et al. . |
| 5,079,142 | 1/1992 | Coleman et al. . |
| 5,079,174 | 1/1992 | Buck et al. . |
| 5,085,987 | 2/1992 | Olson . |
| 5,085,988 | 2/1992 | Olson . |
| 5,087,556 | 2/1992 | Ertinghausen . |
| 5,089,391 | 2/1992 | Buechler et al. . |
| 5,094,956 | 3/1992 | Grow et al. . |
| 5,096,809 | 3/1992 | Chen et al. . |
| 5,096,837 | 3/1992 | Fan et al. . |
| 5,100,619 | 3/1992 | Baker et al. . |
| 5,104,793 | 4/1992 | Buck . |
| 5,104,811 | 4/1992 | Berger et al. . |
| 5,104,812 | 4/1992 | Kurn et al. . |
| 5,106,582 | 4/1992 | Baker . |
| 5,106,758 | 4/1992 | Adler et al. . |
| 5,110,550 | 5/1992 | Schlipfenbacher et al. . |
| 5,114,673 | 5/1992 | Berger et al. . |
| 5,118,428 | 6/1992 | Sand et al. . |
| 5,118,472 | 6/1992 | Tanaka et al. . |
| 5,120,504 | 6/1992 | Petro-Roy et al. . |
| 5,120,643 | 6/1992 | Ching et al. . |
| 5,120,662 | 6/1992 | Chan et al. . |
| 5,130,258 | 7/1992 | Makino et al. . |
| 5,132,208 | 7/1992 | Freitag et al. . |
| 5,135,719 | 8/1992 | Hillman et al. . |
| 5,135,873 | 8/1992 | Patel et al. . |
| 5,137,804 | 8/1992 | Greene et al. . |
| 5,137,808 | 8/1992 | Ullman et al. . |
| 5,141,850 | 8/1992 | Cole et al. . |
| 5,145,784 | 9/1992 | Cox et al. . |
| 5,156,952 | 10/1992 | Litman et al. . |
| 5,156,953 | 10/1992 | Litman et al. . |
| 5,158,869 | 10/1992 | Pouletty et al. . |
| 5,160,486 | 11/1992 | Schlipfenbacher et al. . |
| 5,162,238 | 11/1992 | Eikmeier et al. . |
| 5,164,294 | 11/1992 | Skold et al. . |

| | | | |
|---|---|---|---|
| 5,169,789 | 12/1992 | Bernstein . | |
| 5,171,529 | 12/1992 | Schreiber . | |
| 5,177,021 | 1/1993 | Kondo . | |
| 5,182,191 | 1/1993 | Fan et al. . | |
| 5,185,127 | 2/1993 | Vonk . | |
| 5,188,939 | 2/1993 | Mangold et al. . | |
| 5,188,966 | 2/1993 | Eikmeier et al. . | |
| 5,200,317 | 4/1993 | Georgevich . | |
| 5,200,321 | 4/1993 | Kidwell . | |
| 5,202,268 | 4/1993 | Kuhn et al. . | |
| 5,206,177 | 4/1993 | DeLaCroix et al. . | |
| 5,209,904 | 5/1993 | Forney et al. . | |
| 5,212,060 | 5/1993 | Maddox . | |
| 5,215,713 | 6/1993 | Steinbiss . | |
| 5,223,436 | 6/1993 | Freitag et al. . | |
| 5,232,663 | 8/1993 | Wilk et al. . | |
| 5,232,835 | 8/1993 | Litman et al. . | |
| 5,234,813 | 8/1993 | McGeehan et al. . | |
| 5,238,652 | 8/1993 | Sun et al. . | |
| 5,238,847 | 8/1993 | Steinbiss et al. . | |
| 5,240,862 | 8/1993 | Koenhen et al. . | |
| 5,252,293 | 10/1993 | Drbal et al. . | |
| 5,256,372 | 10/1993 | Brooks et al. . | |
| 5,258,163 | 11/1993 | Krause et al. . | |
| 5,260,193 | 11/1993 | Olson . | |
| 5,260,194 | 11/1993 | Olson . | |
| 5,260,221 | 11/1993 | Ramel et al. . | |
| 5,260,222 | 11/1993 | Patel et al. . | |
| 5,262,067 | 11/1993 | Wilk et al. . | |
| 5,264,180 | 11/1993 | Allen et al. . | |
| 5,273,888 | 12/1993 | Guadagno . | |
| 5,275,785 | 1/1994 | May et al. . | |
| 5,306,623 | 4/1994 | Kiser et al. . | |
| 5,308,580 | 5/1994 | Clark . | |
| 5,308,775 | 5/1994 | Donovan et al. . | |
| 5,314,804 | 5/1994 | Boguslaski . | |
| 5,338,513 | 8/1994 | Schlipfenbacher et al. . | |
| 5,354,692 | 10/1994 | Yank et al. . | |
| 5,364,533 | 11/1994 | Ogura et al. . | |
| 5,395,754 | 3/1995 | Lambotte et al. . | |
| 5,397,479 | 3/1995 | Kass et al. . | |
| 5,401,667 | 3/1995 | Koike . | |
| 5,416,000 | 5/1995 | Allen et al. . | |
| 5,424,220 | 6/1995 | Goerlach-Graw et al. . | |
| 5,435,970 | 7/1995 | Mamenta et al. . | |
| 5,441,698 | 8/1995 | Norell . | |
| 5,451,504 | 9/1995 | Fitzpatrick . | |
| 5,458,852 | 10/1995 | Buechler . | |
| 5,468,647 | 11/1995 | Skold et al. . | |
| 5,468,648 | 11/1995 | Chandler . | |
| 5,491,096 | 2/1996 | Sportsman . | |
| 5,500,375 | 3/1996 | Lee-Own et al. . | |
| 5,504,013 | 4/1996 | Senior . | |
| 5,521,102 | 5/1996 | Boehringer . | |
| 5,540,888 | 7/1996 | Bunce et al. . | |
| 5,547,848 | 8/1996 | Shinoki et al. . | |
| 5,559,041 | 9/1996 | Kang et al. . | |
| 5,569,589 | 10/1996 | Hiraoka et al. . | |
| 5,569,608 | 10/1996 | Sommer . | |
| 5,573,921 | 11/1996 | Behnke et al. . | |
| 5,591,645 | 1/1997 | Rosenstein . | |
| 5,629,164 | 5/1997 | Rivers | 435/7.9 |
| 5,766,962 | 6/1998 | Childs et al. | 436/518 |

FOREIGN PATENT DOCUMENTS

| | | |
|---|---|---|
| 0447154 | 9/1991 | European Pat. Off. . |
| 0516095 | 12/1992 | European Pat. Off. . |
| 0560410 | 9/1993 | European Pat. Off. . |
| 0560411 | 9/1993 | European Pat. Off. . |
| 2016687 | 9/1979 | United Kingdom . |
| 2173304 | 10/1986 | United Kingdom . |
| 2201241 | 8/1988 | United Kingdom . |

| | | | | | |
|---|---|---|---|---|---|
| 2204398 | 11/1988 | United Kingdom . | WO 89/03992 | 5/1989 | WIPO . |
| WO 82/02211 | 7/1982 | WIPO . | WO 89/06801 | 7/1989 | WIPO . |
| WO 84/02193 | 6/1984 | WIPO . | WO 91/01003 | 1/1991 | WIPO . |
| WO 86/03839 | 7/1986 | WIPO . | WO 91/19980 | 12/1991 | WIPO . |
| WO 86/04683 | 8/1986 | WIPO . | WO 92/01226 | 1/1992 | WIPO . |
| WO 87/02774 | 5/1987 | WIPO . | WO 93/03176 | 2/1993 | WIPO . |
| WO 87/02778 | 5/1987 | WIPO . | WO 95/13541 | 5/1995 | WIPO . |

DETACHABLE-ELEMENT ASSAY DEVICE

BACKGROUND OF THE INVENTION

This invention is directed to assay devices for determination of characteristics of samples, unitized housings, and kits incorporating the test strips and housings, and methods of determining the characteristics of samples using test strips and housings, in which the test strips and housings employ detachable components.

Among the many analytical systems used for detection or determination of analytes, particularly analytes of biological interest, are chromatographic assay systems as well as other assay systems employing test strips for detection or determination of analytes.

Among the analytes frequently assayed with such systems are:

(1) hormones, such as human chorionic gonadotropin (hCG), frequently assayed as a marker of human pregnancy;
(2) antigens, particularly antigens specific to bacterial, viral and protozoan pathogens such as Streptococcus, hepatitis virus, and the protozoan Giardia, a frequent cause of diarrhea;
(3) antibodies, particularly antibodies induced as a result of infection with pathogens, such as antibodies to the bacterium *Helicobacter pylori* and to human immunodeficiency virus (H.I.V.), suspected to be the cause of AIDS;
(4) other proteins, such as hemoglobin, frequently assayed in determinations of fecal occult blood, an early indicator of gastrointestinal disorders such as colon cancer;
(5) enzymes, such as aspartate aminotransferase, lactate dehydrogenase, alkaline phosphatase, and glutamate dehydrogenase, frequently assayed as indicators of physiological function and tissue damage;
(6) drugs, both therapeutic drugs, such as antibiotics, tranquilizers, and anticonvulsants, and illegal drugs of abuse, such as cocaine, heroin, marijuana, and methamphetamine;
(7) environmental pollutants such as pesticides and aromatic hydrocarbons;
(8) vitamins; and
(9) other physiologically important compounds such as cholesterol, whose concentration is symptomatic of health or disease states.

Such chromatographic systems and other assay systems involving test strips are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such systems are the "thin layer" systems in which a solvent moves across a thin, flat absorbent medium. Among the most important of tests that can be performed with such thin layer systems are immunoassays, which depend on the specific interaction between an antigen or a hapten and a corresponding antibody. The use of immunoassays as a means of testing for the presence or amount of clinically important molecules has been known for some time. As early as 1956, J. M. Singer reported the use of an immune-based latex agglutination test for detecting a factor associated with rheumatoid arthritis (Singer et al., *Am. J. Med.* 222: 888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen, and if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. The antigen to be detected can itself be an antibody, such as in serological assays for *H. pylori*-specific antibody. In such cases, the antibody to be detected can be bound to a specific antigen. Alternatively, the antigen to be detected can be detected indirectly by using a labeled second antibody that binds to the first antibody to the antigen to be detected.

In general, the sandwich immunochromatographic procedures call for mixing the sample that may contain the analyte to be assayed with antibodies to the analyte. These antibodies are mobile and typically are linked to a label or a disclosing reagent, such as dyed latex, a colloidal metal sol, or a radioisotope. This mixture is then applied to a chromatographic medium containing a band or zone of immobilized antibodies to the analyte of interest. The chromatographic medium often is in the form of a strip resembling a dipstick. When a complex of the molecule to be assayed and the labeled antibody reaches the zone of the immobilized antibodies on the chromatographic medium, binding occurs, and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

In competitive immunoassays, the label is typically labeled analyte or analyte analogue which competes for binding to an antibody with any unlabeled analyte present in the sample. Competitive immunoassays are typically used for detection of analytes such as haptens, each hapten being monovalent and capable of binding only one antibody molecule. Examples of competitive immunoassay devices are those disclosed by U.S. Pat. No. 4,235,601 to Deutsch et al., U.S. Pat. No. 4,442,204 to Liotta, and U.S. Pat. No. 5,208,535 to Buechler et al., all of which are incorporated herein by this reference. Other forms of competitive immunoassays exist using labeled antibody.

Although useful, currently available chromatographic techniques using test strips have a number of drawbacks. Many samples, such as fecal samples, contain particulate matter that can clog the pores of a chromatographic medium, greatly hindering the immunochromatographic process. Other samples, such as blood, contain cells and colored components that make it difficult to read the test. Even if the sample does not create interference, it is frequently difficult with existing chromatographic test devices to apply the sample to the chromatographic medium so that the sample front moves uniformly through the chromatographic medium to ensure that the sample reaches the area where binding is to occur in a uniform, straight-line manner. Similar problems occur with other assay methods employing test strips that do not employ immunochromatography.

Other problems exist with currently-available test strips because of the nature of the sample to be assayed or the assay to be carried out. With such devices, it is impractical to perform washing steps which are frequently desirable to improve sensitivity and to reduce background. Also, it is difficult, and in many cases impossible, to carry out preincubation steps within the device or incubation steps for development of a detectable signal such as that produced by an enzyme label.

Additionally, there is a need for an immunochromatographic assay device that can carry out a broad range of separations as well as similar devices for the performance of other assays not involving immunochromatographic principles.

Sample preparation and waste generation are responsible for other problems with currently-available devices and techniques for immunochromatography and other currently-available test strips. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium or other test strip. Several extraction and pretreatment reactions are usually required before the sample can be applied to the chromatographic medium or the test strip. These reactions are typically carried out by the physician or technician performing the test in several small vessels, such as test tubes or microfuge tubes, requiring the use of transfer devices, such as pipettes. Each of the vessels and transfer devices is then contaminated and must be disposed of, using special precautions so that workers or people who may inadvertently come into contact with the waste do not become contaminated.

Still another limitation on chromatographic devices currently available for use by the clinician or technician is their inability to perform two-directional chromatography. This technique has long been known to be a powerful analytical tool, but its complexity, relative to simple unidirectional chromatography, has made it difficult to apply it to test strip devices in the physician's office or clinical laboratory.

Additional considerations arise from storage requirements for currently available devices. It is well known by those skilled in the art that moisture is detrimental to the stability of an immunochromatographic test device. Therefore, a means of maintaining a low humidity environment is necessary. The entire test device, consisting of the housing and its attached components, is sealed in a barrier bag which is essentially moisture impermeable. Typically, a desiccant such as silica gel, "molecular sieves," or clay-based derivatives is also sealed with the device in order to scavenge residual moisture released by the device itself or moisture which may permeate the barrier over time.

From a functionality standpoint, only the biologically reactive components require a low humidity environment. The non-biologically active components of such a device do not require such an environment. Sealing the entire test device in a low humidity environment is not done out of necessity, rather out of convenience. However, convenience exacts a price. The moisture barrier component must be sufficiently large to accommodate the entire test device. This increases the final package dimensions of test kits incorporating these devices and increases the volume of desiccant required.

In addition to increased packaging and its associated costs, other prices are to be paid for the convenience of a single, unitary device. Assembly times are increased when a test strip containing biologically active components is applied to a housing. The increased time is inversely related to manufacturing throughput and directly related to the cost of the finished test. If the housing is comprised of a material capable of high residual moisture levels, e.g., a cellulosic material such as cardboard, procedures are required to reduce the residual moisture to acceptable levels thereby again increasing manufacturing costs. Also, moisture reduction requires specialized equipment which must be purchased, operated, and maintained, again increasing cost.

Accordingly, there is a need for an improved assay device capable of handling a broad range of chromatographic assays and other assays employing test strips. Such a device should be able to handle all types of immunoassays, including both sandwich and competitive immunoassays, as well as other types of assays using chromatography and other assays involving test strips. Such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the test. Additionally, such an improved test strip should be capable of performing bidirectional chromatography when used in clinical laboratories or physicians' offices. Moreover, such an improved assay device should reduce packaging and storage costs and the volume of desiccant required for storage.

SUMMARY

We have developed an assay device that meets these needs and provides improved assays for analytes of biological interest, while simplifying the performance of the assay, avoiding contamination, and reducing storage costs. The device can perform all types of immunoassays, including sandwich immunoassays, competitive immunoassays, and assays employing combinations of these principles. The device can perform serological assays in which the antigen to be detected is itself an antibody, such as antibody to *H. pylori*. The device can perform assays in which the antigen to be detected is detected indirectly by using a labeled second antibody binding to the first antibody to the analyte.

An assay device, according to the present invention, employs either at least one detachable component or a plurality of hinged panels, as shown in more detail below. An assay device, according to the present invention, makes use of pressure to transfer fluid from one opposable component to another opposable component, and also to drive fluid through the chromatographic medium or other test strip. The pressure not only speeds up the operation of the device, but allows the performance of additional steps, such as extraction steps to remove interfering particulate components or incubation steps to allow the development of a detectable signal by an enzyme label, within a single device. The pressure is generated by holding the opposable components together. Preferably, a predetermined pressure is applied to ensure the optimum performance of each step of the assay procedure.

Additionally, the device can perform other types of specific binding assays, such as: (1) assays based on the affinity of specific binding proteins such as lectins, hormone receptors, or viral receptors for their specific ligands; (2) assays based on the affinity of enzymes for their corresponding substrates or inhibitors, or (3) assays based on the affinity of a nucleic acid (DNA or RNA) segment for a complementary nucleic acid segment according to the Watson-Crick base pairing scheme.

One embodiment of a device according to the present invention comprises:

(1) a first opposable component including:
   (a) a first panel;
   (b) a second panel mounted on the first panel generally parallel to the first panel with space between the first and second panel, the second panel having an opening forming a first receptacle for a sample collection device; and
   (c) a second receptacle for a test strip formed by the first panel and the second panel; and
(2) a second opposable component hingedly attached to the first opposable component.

In this device, the first and second opposable components can be brought into operable contact so that fluid is expressed from the sample collection device and applied to the test strip for detection or determination of an analyte by a test performed on the test strip.

Typically, the first receptacle is shaped to hold a generally ovoid swab.

Typically, the second receptacle is a receptacle that holds a chromatographic medium having a first end and second end such that the chromatographic medium is inserted into the receptacle so that when the first and second opposable components are brought into opposition, the fluid expressed from the sample collection device is applied to the first end of the chromatographic medium.

The second opposable component can include an aperture for viewing of at least a portion of the test strip. When the test strip is a chromatographic medium, it preferably includes a detection zone, and the second opposable component preferably further includes an aperture for viewing of the detection zone.

Another aspect of the present invention is a test kit comprising, in separately packaged containers:

(1) the assay device described above; and
(2) a test strip backed with adhesive and a releasable liner for insertion into the second receptacle of the assay device. The test kit can further comprise, separately packaged, at least one additional reagent for application either to the sample collection device or the test strip. The additional reagent can form an extraction reagent when applied to the sample collection device. The extraction reagent formed can be nitrous acid.

Other embodiments of the present invention can similarly be incorporated into test kits.

Another aspect of the present invention is a method for detection or determination of a analyte comprising the steps of:

(1) collecting a sample on a sample collection device;
(2) inserting the sample collection device containing the sample into the first receptacle of the assay device described above;
(3) removing a releasable liner from a test strip backed with adhesive and a releasable liner and inserting the test strip from which the releasable liner has been removed into the second receptacle of the assay device;
(4) bringing the first and second opposable components of the assay device into opposition to express fluid from the sample collection device for application to the test strip; and
(5) observing or measuring a detectable signal produced on the test strip in response to fluid applied to it in order to detect or determine the analyte on the test strip.

The method can further comprise the step of adding at least one additional reagent to the sample collection device.

Other embodiments of the present invention can also be used in similar assay methods, as indicated below.

Another embodiment of the present invention is an assay device comprising:

(1) a first opposable component including:
   (a) a first panel; and
   (b) an opening forming a first receptacle for a sample collection device in the first panel;
(2) a second opposable component hingedly attachable to the first panel of the first opposable component, the second opposable component including therein an aperture; and
(3) a third opposable component hingedly attachable to the second opposable component, the third opposable component including a second receptacle for a test strip.

In this embodiment, the second and third opposable components are foldable and the first and second opposable components are brought into operable contact when the second opposable component has been folded over the third opposable component so that fluid is expressed from the sample collection device and applied to the test strip for detection or determination of the analyte.

Another embodiment of an assay device according to the present invention comprises:

(1) a first module comprising:
   (a) a first panel, the first panel including therein a receptacle for a sample collection device;
   (b) a second panel hingedly attached to the first panel, the second panel having an aperture for viewing of a portion of a test strip; and
(2) a second module including therein a second receptacle for a test strip, the second module reversibly hingedly attachable to the second panel of the first module.

In this embodiment, when the second module is attached to the first module, the second module is folded over the second panel of the first module, and the second module and the second panel of the first module are folded over the first panel of the first module to bring the second module and the first panel of the first module into operable contact, fluid is expressed from the sample collection device and applied to the test strip for detection or determination of an analyte therein.

Test kits incorporating this device can comprise the first and second modules, packaged separately, along with a test strip and any additional reagents. Alternatively, at least two second modules can be provided, along with a test strip for each second module. This allows flexibility and the performance of one of two or more alternate tests using the same test kit.

Another embodiment of an assay device according to the present invention comprises:

(1) a first support panel including thereon a sample preparation zone;
(2) a second support panel hingedly attached to the first support panel and including therein an aperture, the second support panel shaped to have first, second, third, and fourth sides with the first and third sides being substantially parallel and the second and fourth sides being substantially parallel, with the first side being hingedly attached to the first support panel;
(3) a third support panel hingedly attached to the third side of the second support panel, the third support panel having first and second surfaces with a test strip attached to the second surface;
(4) a first reaction panel hingedly attached to the second side of the second support panel having thereon a first reaction pad; and (5) a second reaction panel hingedly attached to the fourth side of the second support panel having thereon a second reaction pad.

In this device, the third support panel is folded over the second support panel and the combination of the second and third support panels are folded over the first support panel to bring the test strip into operable contact with the sample preparation zone. When the third support panel is folded over the second support panel, the first reaction panel is folded over the third support panel so that the first reaction pad is in operable contact with a first portion of the test strip and the second reaction panel is folded over the third support panel so that the second reaction pad is in operable contact with a second portion of the test strip.

In one alternative, the first reaction pad can include therein an extraction reagent. In another alternative, the first reaction pad can include a labeled specific binding partner for the analyte in resolubilizable form.

In another alternative, the second reaction pad can include therein a labeled specific binding partner for the analyte in resolubilizable form. In still another alternative, the first reaction pad can have a specific binding partner for the analyte in resolubilizable form labeled with a catalyst, and the second reaction pad can have in resolubilizable form at least one compound capable of participating in a reaction catalyzed by the catalyst to produce a detectable signal. Typically, the catalyst is an enzyme. Preferably, the enzyme is horseradish peroxidase, β-galactosidase, glucose oxidase, or alkaline phosphatase.

In another alternative, the first reaction pad contains a specific binding partner labeled with a detectable label in resolubilizable form and the second reaction pad contains an amplifying reagent to amplify a signal produced by the detectable label. Preferably, the detectable label is a gold sol label and the amplification system includes a quinone and a soluble silver salt.

Another embodiment of the present invention is an assay device comprising:
(1) a first module including:
   (a) a first support panel including thereon a sample preparation zone; and
   (b) a second support panel having an aperture therein and having first, second, third, and fourth sides, with the first and third sides and second and fourth sides being generally parallel, the second support panel being hingedly attached to the first support panel via the first side of the second support panel;
(2) a second module comprising a third support panel, the third support panel including thereon a test strip, the second module being removably hingedly attachable to the third side of the second support panel of the first module;
(3) a third module that is a first reaction panel that has a first reaction pad thereon and that is removably hingedly attachable to the second side of the second support panel of the first module; and
(4) a fourth module that is a second reaction panel that has a second reaction pad thereon and that is removably hingedly attachable to the fourth side of the second support panel of the first module.

In this device the second module is folded over the second support panel of the first module and, when the second module is folded over the second support panel of the first module, the second module and the second support panel of the first module are folded over the first support panel of the first module to bring the sample preparation zone into operable contact with the test strip. When the second module is folded over the second support panel of the first module, the third module is folded over the second support panel of the first module and the second module to bring the first reaction pad into operable contact with a first portion of the test strip and the fourth module is folded over the second support panel of the first module and the second module to bring the second reaction pad into operable contact with the second portion of the test strip.

The alternatives for the reagents contained in the reaction pads are the same for this embodiment as for the embodiment in which the reaction pads are not removably attached.

Another embodiment of an assay device according to the present invention comprises:
(1) a first support panel including thereon a sample preparation zone;
(2) a second support panel hingedly attached to the first support panel and including therein an aperture, the second support panel shaped to have first, second, third, and fourth sides with the first and third sides being substantially parallel and the second and fourth sides being substantially parallel, with the first side being hingedly attached to the first support panel;
(3) a third support panel hingedly attached to the third side of the second support panel, the third support panel having first and second surfaces and having a receptacle for a test strip such that, when a test strip is inserted into the receptacle, a surface of the test strip is accessible from the second surface of the third support panel;
(4) a first reaction panel hingedly attached to the second side of the second support panel having thereon a first reaction pad; and
(5) a second reaction panel hingedly attached to the fourth side of the second support panel having thereon a second reaction pad.

In this embodiment, the third support panel is folded over the second support panel and the combination of the second and third support panels can be folded over the first support panel to bring the test strip into operable contact with the sample preparation zone. When the third support panel is folded over the second support panel, the first reaction panel is folded over the third support panel so that the first reaction pad is in operable contact with a first portion of the test strip and the second reaction panel can be folded over the third support panel so that the second reaction pad is in operable contact with a second portion of the test strip.

Another embodiment of an assay device according to the present invention comprises:
(1) a first module including:
   (a) a first support panel including thereon a sample preparation zone; and
   (b) a second support panel having an aperture therein and having first, second, third, and fourth sides, with the first and third sides and second and fourth sides being generally parallel, the second support panel being hingedly attached to the first support panel via the first side of the second support panel;
(2) a second module comprising a third support panel, the third support panel having first and second surfaces and having a receptacle for a test strip such that, when a test strip is inserted into the receptacle, a surface of the test strip is accessible from the second surface of the third support panel, the second module being removably hingedly attachable to the third side of the second support panel of the first module;
(3) a third module that is a first reaction panel that has a first reaction pad thereon and that is removably hingedly attachable to the second side of the second support panel of the first module; and (4) a fourth module that is a second reaction panel that has a second reaction pad thereon and that is removably hingedly attachable to the fourth side of the second support panel of the first module.

In this device, the second module is folded over the second support panel of the first module and, when the second module is folded over the second support panel of the first module, the second module and the second support panel of the first module are folded over the first support panel of the first module to bring the sample preparation zone into operable contact with the test strip. When the second module is folded over the second support panel of the first module, the fourth module is folded over the second support panel of the first module and the second module to bring the first reaction pad into operable contact with a first portion of the test strip and the second reaction panel is folded over the second support panel of the first module and the second module to bring the second reaction pad into operable contact with the second portion of the test strip.

Yet another embodiment of an assay device according to the present invention comprises:

(1) a first opposable component including:
  (a) a first panel;
  (b) a second panel mounted on the first panel generally parallel to the first panel with space between the first and second panel, the second panel having an opening forming a first receptacle for a sample collection device;
  (c) a second receptacle for a test strip formed by the first panel and the second panel, the second receptacle having slidable contact means to hold the test strip slidably in one of two positions, a first position in which the test strip is in operable contact with a sample collection device placed in the first receptacle and a second position in which the test strip is not in operable contact with the sample collection device; and
  (d) a test strip in the second receptacle; and
(2) a second opposable component hingedly attached to the first opposable component.

In this embodiment of the device, the first and second opposable components are brought into operable contact so that fluid is expressed from the sample collection device and applied to the test strip when the test strip is in the first position for detection or determination of an analyte by a test performed on the test strip.

BRIEF DESCRIPTION OF THE DRAWINGS

These and other features, aspects, and advantages of the present invention will become better understood with reference to the following description, appended claims, and accompanying drawings where:

DEFINITIONS

Figure 1:
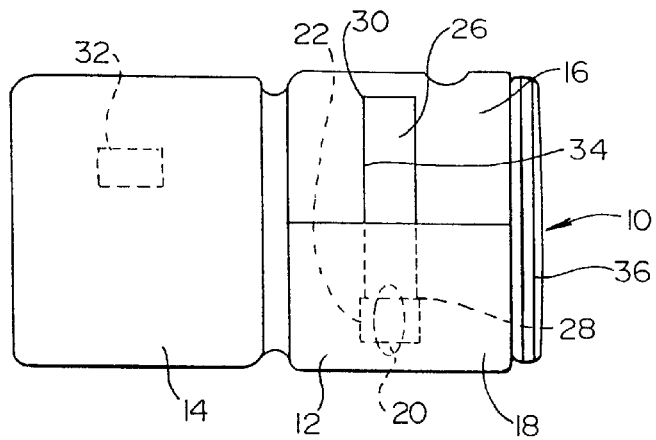
FIG. 1 is a drawing of a first embodiment of an assay device according to the present invention.

In the context of this disclosure, the following terms are defined as follows unless otherwise indicated:

Specific binding partner: a member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable contact: Two solid components are in operable contact when they are in contact, either directly or indirectly, in such a manner that an aqueous liquid can flow from one of the two components to the other substantially uninterruptedly, by capillarity or otherwise. "Direct contact" means that the two elements are in physical contact, such as edge-to-edge or front-to-back. Typically, when two components are in direct contact, they are overlapped with an overlap of about 0.5 mm to about 3 mm. However, the components can be placed with abutting edges. "Indirect contact" means that the two elements are not in physical contact, but are bridged by one or more conductors.

Analyte: The term "analyte" includes both the actual molecule to be assayed and analogues and derivatives thereof, when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), Fv, and F(ab')$_2$ fragments), as well as chemically modified intact antibody molecules and antibody fragments such as Fv fragments, including hybrid antibodies assembled by in vitro reassociation of subunits. The term also encompasses both polyclonal and monoclonal antibodies. Also included are genetically engineered antibody molecules such as single-chain antibody molecules, generally referred to as sFv. The term "antibody" also includes modified antibodies or antibodies conjugated to labels or other molecules that do not block or alter the binding capacity of the antibody.

Secondary specific binding partner: An additional specific binding partner that binds to a member of a pair of specific binding partners when the pair of specific binding partners is interacting is designated a secondary specific binding partner. For example, a pair of specific binding partners can comprise Giardia antigen and rabbit anti-Giardia antibody. In that case, the secondary specific binding partner can be goat anti-rabbit Ig antibody. The secondary specific binding partner can be specific for the species, class, or subclass of an antibody specific binding partner to which it binds. Alternatively, when one of the specific binding partners is labeled with biotin, the secondary specific binding partner can comprise a molecule conjugated to avidin.

I. ASSAY DEVICES

Assay devices according to the present invention either employ at least one detachable element or employ a plurality of hinged panels to carry out reaction steps. In one alternative, both detachable elements and the use of hinged panels are employed to carry out a plurality of reaction steps within a unitary device.

A. Two-Component Device with Insertable Test Strip

One embodiment of a device according to the present invention is a two-component device with an insertable test strip. This device is shown in FIG. 1.

The device 10 has a first opposable component 12 and a second opposable component 14. The second opposable component 14 is hingedly attached to the first opposable component 12. The first opposable 12 component includes a first panel 16 and a second panel 18. The second panel 18 is mounted on the first panel 16 generally parallel to the first panel 16 with space between the first and second panels 16 and 18. The second panel 18 has an opening forming a first receptacle 20 for a sample collection device. A second receptacle 22 for a test strip is formed by the first panel 16 and the second panel 18.

In the operation of the device, the first and second opposable components 12 and 14 are brought into operable contact so that fluid is expressed from the sample collection device and applied to the test strip for detection or determination of an analyte by a test performed on the test strip.

Typically, the first receptacle 20 is shaped to hold a generally ovoid swab as the sample collection device.

Typically, the test strip is a chromatographic medium, such as chromatographic medium 26 shown in FIG. 1, having a first end 28 and a second end 30. The chromatographic medium 26 is inserted into the second receptacle in such a way so that when the first and second opposable components 12 and 14 are brought into opposition with the chromatographic medium 26 in the device, fluid expressed from the sample collection device is applied to the first end 28 of the chromatographic medium 26.

Typically, the second opposable component 14 includes an aperture 32 for viewing of at least a portion of the test strip. Typically, the chromatographic medium 26 further includes a detection zone 34 and the aperture 32 in the second opposable component 14 is for viewing of the detection zone 34. The device can further comprise sealing means such as the closure 36 to hold the first and second opposable components 12 and 14 in opposition. Preferably, the closure 36 is in such an orientation that it allows insertion of the chromatographic medium 26 after the first and second opposable components 12 and 14 are brought into opposition.

The test strip, typically a chromatographic medium, is preferably backed with adhesive and a releasable liner for insertion into the second receptacle 22 of the assay device.

Details of construction of this device are given below. Unless otherwise indicated, these details also apply to other embodiments of the device to be discussed further below.

The chromatographic medium is a strip. Typically, the strip is substantially planar, although this is not required for all applications. It is typically rectangular, having first and second ends and first and second surfaces. Throughout this description, the term "first end" refers to the end at or near which liquid is first applied to the chromatographic medium and the term "second end" refers to the opposite end of the chromatographic medium. The liquid applied at or near the first end of the chromatographic medium can be, but is not necessarily, a sample, a treated sample, or material contained in a sample collection device such as a swab. The chromatographic medium is composed of material suitable as a medium for thin layer chromatography of analyte and analyte-antibody conjugates, such as nitrocellulose, nylon, rayon, cellulose, paper, or silica. The chromatographic medium can be pretreated or modified as needed. Typically, the chromatographic medium is translucent, so that colored zones appearing on it can be viewed from either side.

Typically, particularly when used for sandwich immunoassays, the chromatographic medium has a detection zone of immobilized specific binding partner to the analyte thereon. Typically, the detection zone is substantially smaller than the chromatographic medium. The immobilized specific binding partner can be bound to the chromatographic medium by either covalent or non-covalent means; covalent means are generally preferred. Methods for immobilizing specific binding partners, particularly antibodies, to chromatographic media are well known in the art and need not be described further here; such methods are described, for example, in P. Tijssen, "Practice and Theory of Enzyme Immunoassays" (Elsevier, Amsterdam, 1985), ch. 13, pp. 297–328.

If the analyte to be assayed is an antigen or hapten, the immobilized specific binding partner is typically an antibody to the antigen or the hapten. Alternatively, the analyte can be an antibody and the specific binding partner that is immobilized can be a hapten or an antigen capable of being bound specifically by the antibody.

Many of the embodiments of the assay device according to the present invention comprise two or three opposable components. The bodies of the opposable components are preferably made of laminated cardboard that is sufficiently impervious to moisture to contain the liquids involved in the performance of the assay carried out by the device. Other cellulose-based materials, such as paperboard or solid bleached sulfite (SBS), can also be used. Alternatively, the bodies of the opposable components can be made of plastic that is impervious to moisture. A suitable plastic is a polycarbonate plastic such as LEXAN™.

The opposable components are hingedly attachable. Typically, the components are joined by a hinge, preferably made of a material impermeable to liquids, such as a plastic that can be compatibly joined with or is the same as the material used for the first and second opposable components.

Typically, devices according to the present invention employ a labeled component to give a detectable signal on the chromatographic medium or other test strip. For assay devices intended to perform a sandwich immunoassay, the labeled component is typically a labeled specific binding partner to the analyte. This labeled component is typically mobile, in that it can migrate through the chromatographic medium, whether free or bound to analyte. The label is preferably a visually detectable label, such as a colloidal metal label. Preferably, the colloidal metal label is gold, silver, bronze, iron, or tin; most preferably, it is gold. The preparation of gold labeled antibodies and antigens is described in J. DeMey, "The Preparation and Use of Gold Probes," in *Immunocytochemistry: Modern Methods and Applications* (J. M. Polak and & S. Van Noorden, eds., Wright, Bristol, England, 1986) ch. 8, pp. 115–145, incorporated herein by this reference. Antibodies labeled with colloidal gold are commercially available, such as from Sigma Chemical Company, St. Louis, Mo.

Alternatively, other colloidal labels, such as a colloidal sulfur label or a dye-silica label, can also be used. In a less preferred alternative, the visually-detectable label can be a colored latex label.

It is also possible to use other labels, such as a radioactive label, a fluorescent label, a chemiluminescent label, or an enzyme label. As discussed below, in certain embodiments of the invention, an enzyme label is in fact preferred.

In general, a method for use of this device for detection or determination of an analyte comprises:
(1) collecting a sample on a sample collection device;
(2) inserting the sample collection device containing the sample into the first receptacle of the assay device;
(3) removing a releasable liner from a test strip backed with adhesive and a releasable liner and inserting the test strip from which the releasable liner has been removed into the second receptacle of the assay device; and
(4) bringing the first and second opposable components of the assay device into opposition to express fluid from the sample collection device for application to the test strip; and
(5) observing or measuring a detectable signal produced on the test strip in order to detect or determine the analyte on the test strip.

Alternatively, the test strip can be inserted after the closure of the first and second opposable components. In some versions of the device, this order of operation is preferable.

After the first and second opposable components are brought into opposition, and fluid is expressed from the sample collection device for application to the test strip, a detectable signal is produced on the test strip. One particularly preferred alternative, a sandwich immunoassay, is performed with a mobile label such as a colloidal gold label that is bound to a specific binding partner for the analyte and an immobilized second specific binding partner for the analyte at a detection zone on the chromatographic medium. When the analyte is present in the sample, and a directly visible label is used, a zone or band of label appears on the chromatographic medium and can be distinguished from the surrounding lighter background, thus indicating the presence of the analyte.

Other additional reagents can be added to the sample collection device. If the mobile labeled specific binding partner for the analyte is not incorporated within the device in resolubilizable form, the mobile labeled specific binding partner for the analyte can be added to the sample collection device. Alternatively, an extraction reagent such as nitrous acid can be added to or formed in the sample collection device. Nitrous acid can be formed by adding acetic acid to sodium nitrite, present in dried form on the sample collection device. Other reagents can be added to the sample collection device. These reagents can include, but are not limited to, acids or alkalis to adjust the pH, buffers to stabilize the pH, chelating agents such as EDTA or EGTA to chelate metals, hydrolytic enzymes to lyse the cell membrane of animal cells or the cell wall of bacteria to liberate analytes, substrates or coenzymes for enzymes, and the like.

Typically, the components are secured to the bodies of the first and second opposable components 12 and 14 by adhesive. Suitable adhesives are well known in the art. Other joining methods, such as stapling or tacking, can also be used.

The assay devices can further incorporate a backing for the test strip between the opposable component and the test strip. The backing can be a thin impermeable plastic.

Assay methods using a device according to the present invention can give a qualitative, semi-quantitative, or quantitative indication of analyte presence or concentration, depending upon the concentration of the labeled specific binding partner at the detection zone and the size of the detection zone, as well as the detection method used. In general, in the specification, the term "detect" is used to refer to a qualitative indication of the presence or absence of an analyte, while the term "determine" is used to refer to either a semi-quantitative or a quantitative determination of the concentration of the analyte. The term "observe" is typically used to refer to a visual observation leading to a qualitative or semi-quantitative determination or detection of analyte presence or concentration, while the term "measure" is typically used to refer to an instrumental measurement that yields a quantitative determination of analyte concentration. Such a measurement is typically by spectroscopy, although other methods can be used.

Typically, to achieve results, the assay requires from about 30 seconds to about 10 minutes, more typically from about 1 to about 5 minutes, including any period of incubation of the sample in the sample collection device, as well as the time required for chromatography itself. Typically, the assay is performed at room temperature, although it can be performed at 4° C. or up to 37° C. or higher in some cases, depending upon the nature of the analyte and the specific binding partners employed. In some cases, performing the assay at a lower temperature may be desirable to limit degradation of the analyte or of another component involved in the reaction. In other cases, performing the assay at a higher temperature with suitable analytes and specific binding partners may speed up the assay. As one alternative in performing certain tests for analytes not involving pathogens or poisonous substances, during the performance of the assay, if the test procedure warrants, the test strip can be removed from the second receptacle and inserted into a heating device such as a microwave heater, to heat the test strip and speed the assay or otherwise treat the sample, such as to perform an extraction. Additionally, the separable test strip, once developed, can be removed from the device for insertion into a reading device such as a spectrophotometer to assist in the quantitation of the result. In general, however, this alternative, involving removal of the strip from the assay device, is not preferred.

B. Three-Component Assay Device

Figure 2:
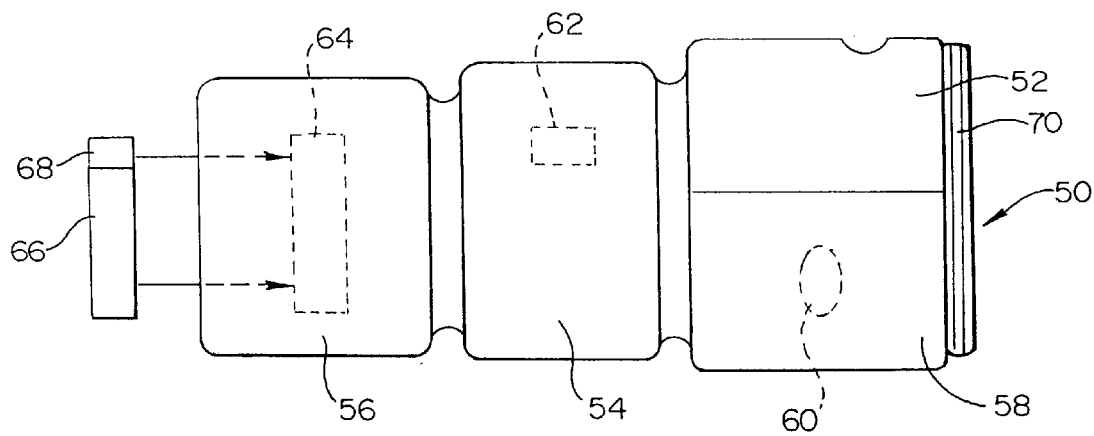
FIG. 2 is a drawing of a second embodiment of an assay device according to the present invention with three opposable components.

A device with a similar construction, but with three opposable components, is shown in FIG. 2. In this device, the first opposable component holds the sample collection device, the second opposable component has an aperture for viewing of the test strip, and the third opposable component holds the test strip.

The device is shown in FIG. 2. The device 50 has a first opposable component 52, a second opposable component 54, and a third opposable component 56. The first opposable component 52 includes a first panel 58 and an opening forming a first receptacle 60 for a sample collection device in the first panel 58. The second opposable component 54 includes therein an aperture 62. The second opposable component 54 is hingedly attachable to the first opposable component 52. The third opposable component 56 is hingedly attachable to the second opposable component 54. The third opposable component 56 includes a second receptacle 64 for a test strip as described above. The second and third opposable components 54 and 56 are foldable. The first and third opposable components 52 and 56 can be brought into operable contact when the third opposable component 56 is folded over the second opposable component 54 and together are folded over the first opposable component 52 so that fluid is expressed from the sample collection device inserted into the first receptacle 60 and applied to the test strip for detection or determination of the analyte.

The aperture 62 is for viewing of a portion of the test strip 66, Typically, the test strip 66 is a chromatographic medium having a detection zone 68; in this case, the aperture 62 allows viewing of the detection zone 68.

Optionally, but preferably, the device includes sealing means such as a closure 70 to hold the three opposable components 52, 54, and 56 into position and seal the test device 50.

Other details of construction of this device are as described above.

An assay for an analyte using this embodiment of the device is performed as follows:
(1) providing a sample collection device containing a sample;
(2) inserting the sample collection device containing the sample into the first receptacle of the assay device;
(3) removing a releasable liner from a test strip backed with adhesive and a releasable liner and inserting the test strip from which the releasable liner has been removed into the second receptacle of the assay device;
(4) folding the third opposable component over the second opposable component;
(5) folding the second and third opposable components together over the first opposable component so that the sample collection device comes into operable contact with the test strip to apply the sample to the test strip; and
(6) observing or measuring a detectable signal produced on the test strip in order to detect or determine the analyte on the test strip.

C. Three-Component Device With Removably Attachable Module for Test Strip

Another alternative embodiment of assay devices according to the present invention, is a three-component device with a removably attachable module for the test strip.

Figure 3:
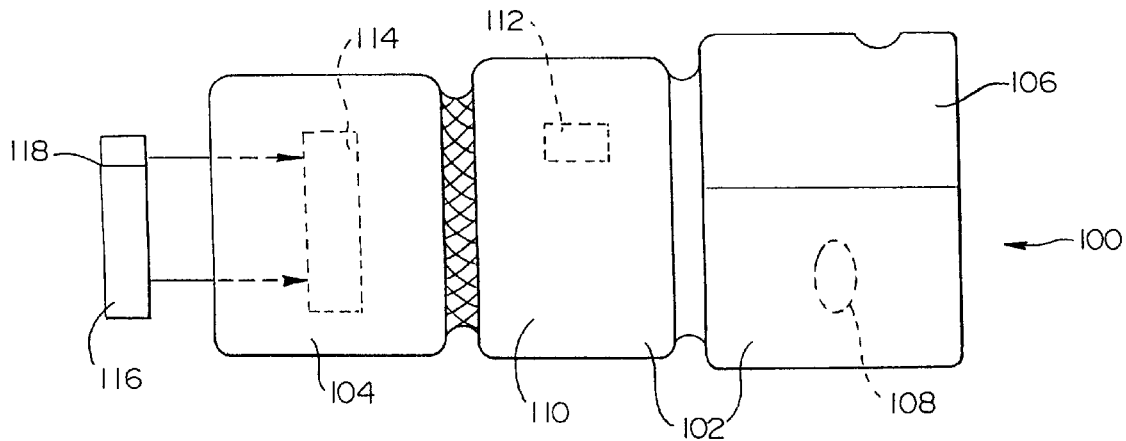
FIG. 3 is a drawing of a third embodiment of an assay device according to the present invention with a removably attachable module for the test strip.

This device is shown in FIG. 3. The device 100 comprises a first module 102 and a second module 104. The first module 102 includes a first panel 106, including therein a first receptacle 108 for a sample collection device as described above. The first module 102 further includes a second panel 110 hingedly attached to the first panel 106. The second panel 110 has an aperture 112 for viewing of a portion of a test strip. The second module 104 includes therein a second receptacle 114 for a test strip 116. The second module 104 is removably hingedly attachable to the second panel 110 of the first module 102. When the second module 104 is attached to the first module 102, the second module 104 is folded over the second panel 110 of the first module 102, and the second panel 110 of the first module 102 and the second module 104 are folded over the first panel 106 of the first module 102 to bring the second module 104 and the first panel 106 of the first module 102 into operable contact, fluid is expressed from a sample collection device inserted into the first receptacle 108 and applied to the test strip 116 for detection or determination of an analyte.

The first receptacle 108 is typically shaped to hold a generally ovoid swab.

The test strip 116 inserted into the second receptacle 114 is typically a chromatographic medium as described above. The chromatographic medium can include a detection zone 118. In this case, the aperture 112 of the second panel 110 of the first module 102 allows viewing of the detection zone 118 when the second module 104 is folded over the second panel 110 of the first module 102.

The first and second modules 102 and 104 are removably hingedly attachable so that the first and second modules 102 and 104 can be detached from each other; it is then possible to generate various combinations of first and second modules 102 and 104. Various means of removably hingedly attaching the first module 102 to the second module 104 can be used. These include the use of removably attachable fabric such as VELCRO™ or a hook-and-eye arrangement. Alternatively, these modules can be removably attached by magnetic or electrical forces. Other means for removably attaching the first and second modules 102 and 104 are well-known in the art and need not be described further here.

This embodiment of the assay device is used as follows:
(1) providing a sample in a sample collection device;
(2) inserting the sample collection device into the first receptacle of the first panel of the first module of the assay device;
(3) removing a releasable liner from a test strip backed with adhesive and a releasable liner and inserting the test strip from which the releasable liner has been removed into the second receptacle in the second module of the assay device;
(4) attaching the second module of the assay device including the test strip to the second panel of the first module of the assay device;
(5) folding the second module of the assay device over the second panel of the first panel of the assay device;
(6) folding the second module and second panel of the first module of the assay device over the first panel of the first module of the assay device to place the test strip into operable contact with the sample collection device so that fluid is expressed from the sample collection device and applied to the test strip; and
(7) observing or measuring a detectable signal produced on the test strip for detection or determination of an analyte on the test strip.

D. Assay Device with Plurality of Hinged Reaction Panels

Another embodiment of an assay device according to the present invention employs a plurality of hinged reaction panels. Each panel includes a reaction pad containing a component that can perform a unique function.

Figure 4:
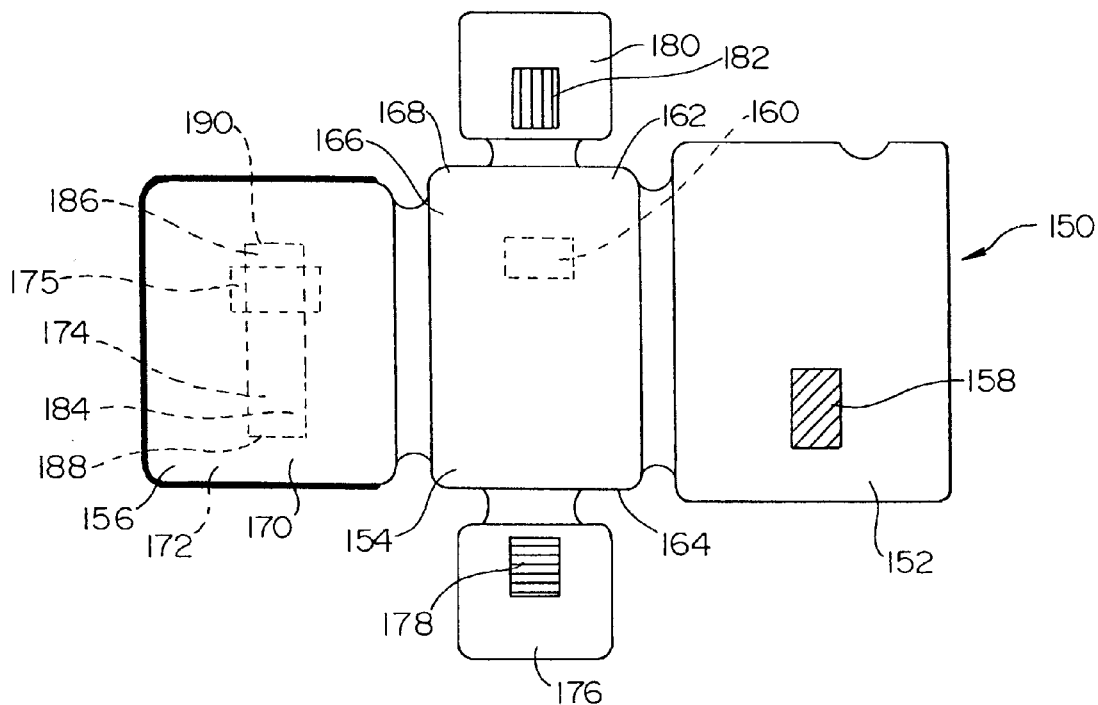
FIG. 4 is a drawing of a fourth embodiment of an assay device according to the present invention with a plurality of hinged reaction panels.

This device is shown in FIG. 4. The device 150 comprises a first support panel 152, a second support panel 154, and a third support panel 156. The first support panel 152 includes thereon a sample preparation zone 158. The second support panel 154 is hingedly attached to the first support panel 152. The second support panel 154 includes therein an aperture 160. The second support panel 154 is shaped to have first, second, third, and fourth sides 162, 164, 166, and 168 with the first and third sides 162 and 166 being substantially parallel, and the second and fourth sides 164 and 168 being substantially parallel. The first side 162 is hingedly attached to the first support panel 152. The third support panel 156 is hingedly attached to the third side 166 of the second support panel 154. The third support panel 156 has first and second surfaces 170 and 172, with a test strip 174 attached to the second surface 172, and can also have an aperture 175 for viewing of the test strip 174.

The device further comprises a first reaction panel 176 hingedly attached to the second side 164 of the second support panel 154. The first reaction panel 176 has thereon a first reaction pad 178.

The device further comprises a second reaction panel 180 hingedly attached to the fourth side 168 of the second support panel 154. The second reaction panel 180 has thereon a second reaction pad 182. The third support panel 156 is folded over the second support panel 154 and the combination of the second and third support panels 154 and 156 are then folded over the first support panel 152 to bring the test strip 174 into operable contact with the sample preparation zone 158. When the third support panel 156 is folded over the second support panel 154, the first reaction panel 176 is folded over the third support panel 156 so that the first reaction pad 178 is in operable contact with the first portion 184 of the test strip, and the second reaction panel 180 is folded over the third support panel 156 so that the second reaction pad 182 is in operable contact with the second portion 186 of the test strip 174.

Typically, the test strip 174 is a chromatographic medium and has first and second ends 188 and 190. The first reaction pad 178 is in operable contact with the first end 188 of the chromatographic medium, and the second reaction pad 182 is in operable contact with the second end 190 of the chromatographic medium.

The first and second reaction pads 178 and 182 can include various combinations of reagents, such as extraction reagents, a labeled specific binding partner for the analyte in resolubilizable form, or a specific binding partner for the analyte in resolubilizable form that is labeled with a catalyst. For example, the first reaction pad 178 can include therein an extraction reagent, such as sodium nitrite to produce nitrous acid when acetic acid is added.

The first reaction pad 178 can alternatively include a labeled specific binding partner for the analyte in resolubilizable form, such as a gold-labeled antibody. Alternatively, the second reaction pad 182 can include therein a labeled specific binding partner for the analyte in resolubilizable form. This alternative is particularly suitable for performing bidirectional immunoassays such as are preferred in a serological assay for the detection of an antibody.

In one alternative, the first reaction pad 178 has a specific binding partner for the analyte in resolubilizable form labeled with a catalyst, and the second reaction pad 182 has in resolubilizable form at least one compound capable of participating in a reaction catalyzed by the catalyst to product a detectable signal. Typically, the catalyst is an enzyme. The enzyme can be any of horseradish peroxidase, β-galactosidase, glucose oxidase, and alkaline phosphatase. Other enzymes are well known as suitable for enzyme immunoassay and can be used. Alternatively, a cascade of two or more enzymes can be used with the product of one enzyme being utilized in a reaction catalyzed by a second enzyme.

In yet another alternative, the first reaction pad 176 can contain a specific binding partner labeled with a detectable label in resolubilizable form and the second reaction pad 182 can contain an amplifying reagent to amplify a signal produced by the detectable label. One particularly useful amplification method is amplification of colloidal gold staining with silver. Silver can be used to amplify colloidal gold as a label for a compound participating in a specific binding reaction. Gold can catalyze the reaction of a soluble silver salt to metallic silver, producing silver shells that surround the gold label so that larger areas are visible. This amplifies the signal that is bound, for example, in a ternary complex at the detection zone when a sandwich immunoassay is used. The soluble silver salt is preferably silver lactate. The reducing agent is typically a quinone, such as hydroquinone. Other amplification techniques are also known in the art.

Alternatively, the second reaction pad 182 can be used to apply a wash liquid such as a buffer or salt solution in the second direction of chromatography. In such case, the appropriate buffers or salts can be incorporated on the second reaction pad 182 in resolubilizable form.

The sample preparation zone 158 can be made of any suitable material, such as, but not limited to, cellulose, paper, nylon, rayon, glass fiber, fleeces, or non-woven synthetic fabrics. A typical material for the sample preparation zone 158 is a bibulous paper such as filter paper.

The porosity of the sample preparation zone 158 can be chosen to filter out cellular or particulate matter in samples such as whole blood or fecal samples. The sample preparation zone can contain at least one reagent for treatment of the sample before the sample is applied to the test strip. Typically, the sample preparation zone 158 is adapted to receive a liquid sample. As used herein, the term "liquid sample" is defined to mean a sample having sufficient liquid so the chromatography can be performed, and includes semisolid samples or samples containing particulate matter. The reagents can be present in the sample preparation zone 158 with the sample to be applied to the sample preparation zone and vary with the analyte to be assayed. They can include, but are not limited to, acids or alkalis to adjust the pH, buffers to stabilize the pH, chelating agents such as EDTA or EGTA to chelate metals, hydrolytic enzymes to lyse the cell membrane of animal cells or the cell wall of bacteria to liberate analytes, substrates or coenzymes, and the like. One particularly useful extraction reagent is a mixture of sodium nitrite and acetic acid to generate nitrous acid. The sodium nitrite can be present in dried form on the sample preparation zone, and the acetic acid can be added to the sample preparation zone before or after the addition of the sample.

In use, a sample is applied to the sample preparation zone 158. Other reagents can also be applied to the sample preparation zone before the sample, simultaneously with the sample, or after the sample. The third support panel 156 is then folded back over the second support panel 154 and the folded third and second support panels 156 and 154 are then folded over the first support panel 152 to bring the sample preparation zone 158 into operable contact with the test strip 174, which is typically a chromatographic medium. This applies the sample and any other reagents applied to the sample preparation zone 158 to the test strip 174. The first support panel 152 is then folded away from the second and third support panels 154 and 156 and the first and second reaction panels 176 and 180 are then folded over the third support panel 156 to bring the first and second reaction pads 178 and 182 into operable contact with portions of the test strip as described above. Depending upon the reagents incorporated in the first and second reaction pads 178 and 182 and the reaction sequence chosen, either the first 176 or the second 180 reaction panel can be folded first to bring it into operable contact with the test strip 174.

Figure 5:
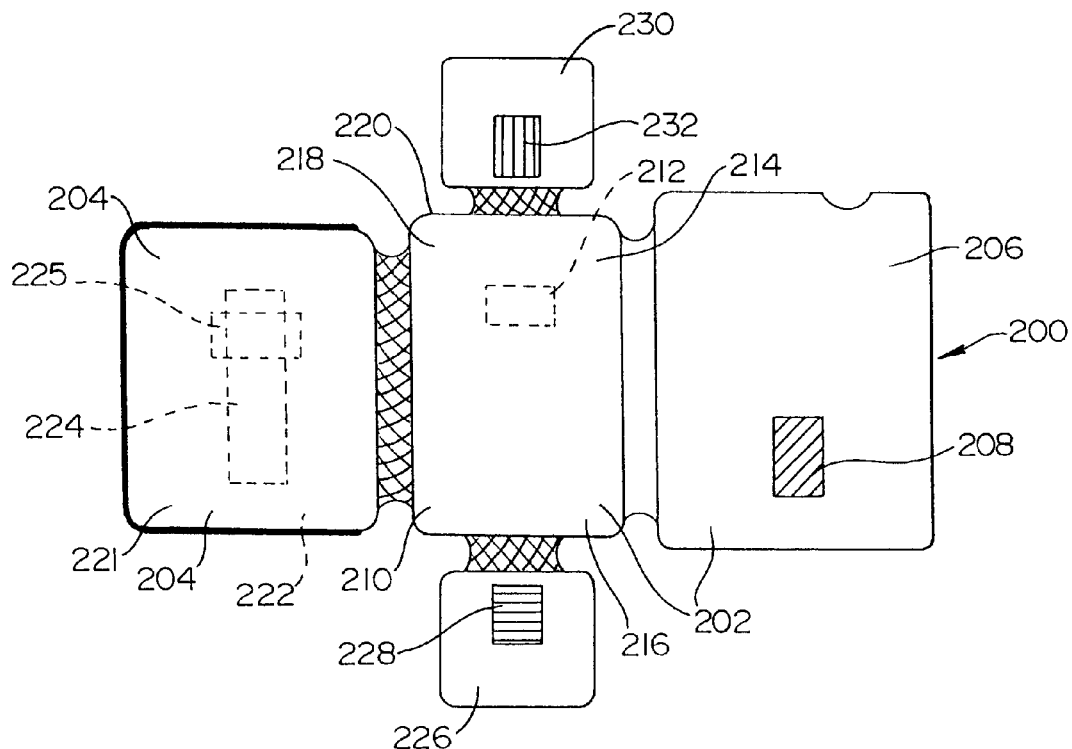
FIG. 5 is a drawing of a fifth embodiment of an assay device according to the present invention with both a plurality of hinged reaction panels and removably attachable modules.

E. Assay Device With Multiple Hinged Panels and Removably Attachable Modules A variant of the embodiment shown in FIG. 4 uses removably hingedly attachable modules for the test strip and the first and second reaction panels. This device is shown in FIG. 5.

The device 200 includes a first module 202 and a second module 204. The first module 202 includes a first support panel 206 including thereon a sample preparation zone 208. The first module 202 also has a second support panel 210 having an aperture therein 212 with first, second, third, and fourth sides 214, 216, 218, and 220. The second support panel 210 is hingedly attached to the first support panel 206 via the first side 214 of the second support panel 210.

The second module 204 comprises a third support panel with first and second surfaces 221 and 222. The third support panel includes thereon a test strip 224 on the second surface 222 of the third support panel. The second module 204 is removably hingedly attachable to the third side 218 of the second support panel 210 of the first module 202. The second module 204 also can include an aperture 225 to allow viewing of the test strip 224.

The device further comprises a third module 226 that is a first reaction panel having a first reaction pad 228 thereon and that is removably hingedly attachable to the second side 216 of the second support panel 210 of the first module 202. The device further comprises a fourth module 230 that is a second reaction panel that has a second reaction pad 232 thereon and that is removably hingedly attachable to the fourth side 220 of the second support panel 210 of the first module 202. This device operates exactly as the device shown in FIG. 4 except for the removably hingedly attachable components.

F. Device With Plurality of Hinged Panels and Insertable Test Strip

An other embodiment of the device is substantially similar to that shown in FIG. 4 but instead of a test strip permanently mounted on the third support panel, it has a receptacle for a test strip. Typically, in the use of this device, a test strip back ed with adhesive and a releasable liner is provided. The releasable liner is removed and the test strip is inserted into the receptacle.

Figure 6:
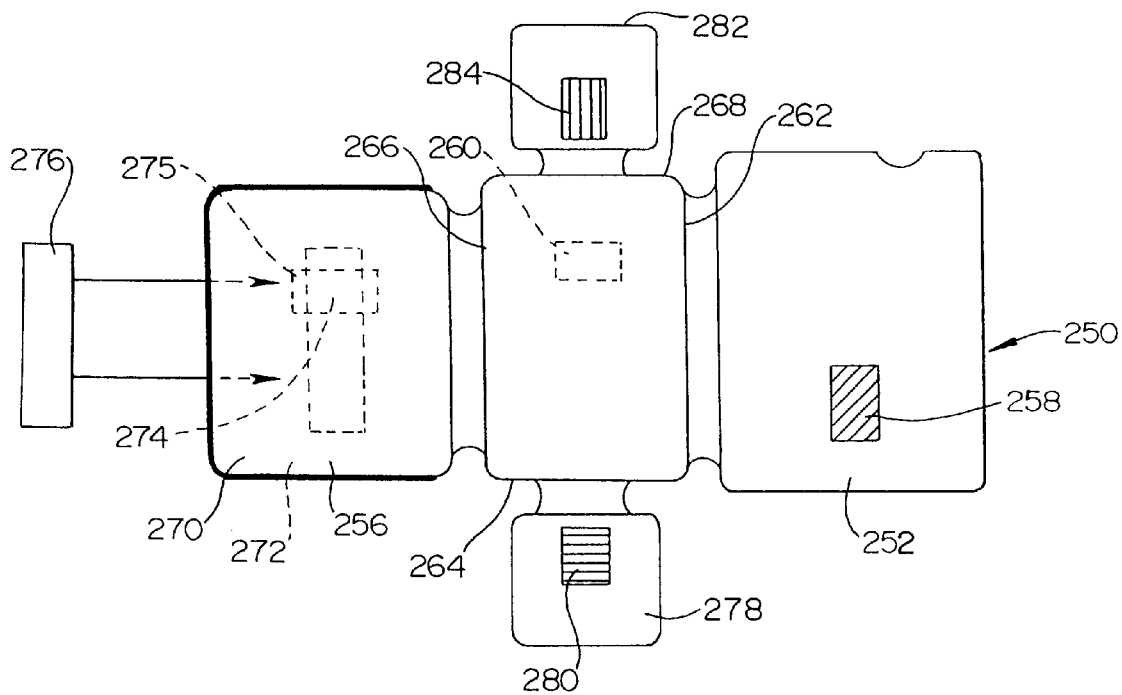
FIG. 6 is a drawing of a sixth embodiment of an assay device according to the present invention with a plurality of hinged reaction panels and a receptacle for a test strip.

This device is shown in FIG. 6. The device 250 has a first support panel 252, a second support panel 254, and a third support panel 256. The first support panel 252 has thereon a sample preparation zone 258 as described above. The second support panel 254 is hingedly attachable to the first support panel 252 and has an aperture 260. The second support panel 254 is shaped to have first, second, third, and fourth sides 262, 264, 266, and 268, as described above. The first side 262 is hingedly attached to the first support panel 252. The third support panel 256 is hingedly attached to the third side 266 of the second support panel 254. The third support panel 256 has first and second surfaces 270 and 272 and has a receptacle 274 for a test strip 276 so that when a test strip is inserted into the receptacle 274, the surface of the test strip 276 is accessible from the second surface 272 of the third support panel 256. The third support panel 256 has an aperture 295. The device further comprises a first reaction panel 278 hingedly attached to the second side 264 of the second support panel 254 and having thereon a first reaction pad 280. The device further comprises a second reaction panel 282 hingedly attached to the fourth side 268 of the second support panel 254 and having thereon a second reaction pad 284.

This device is used exactly as is the device of FIG. 4, except that a test strip is inserted into the receptacle at the appropriate time during the performance of the assay. This can be either before or after the addition of the sample to the sample preparation zone.

G. Device With Detachable Hinged Panels and Insertable Test Strip

Figure 7:
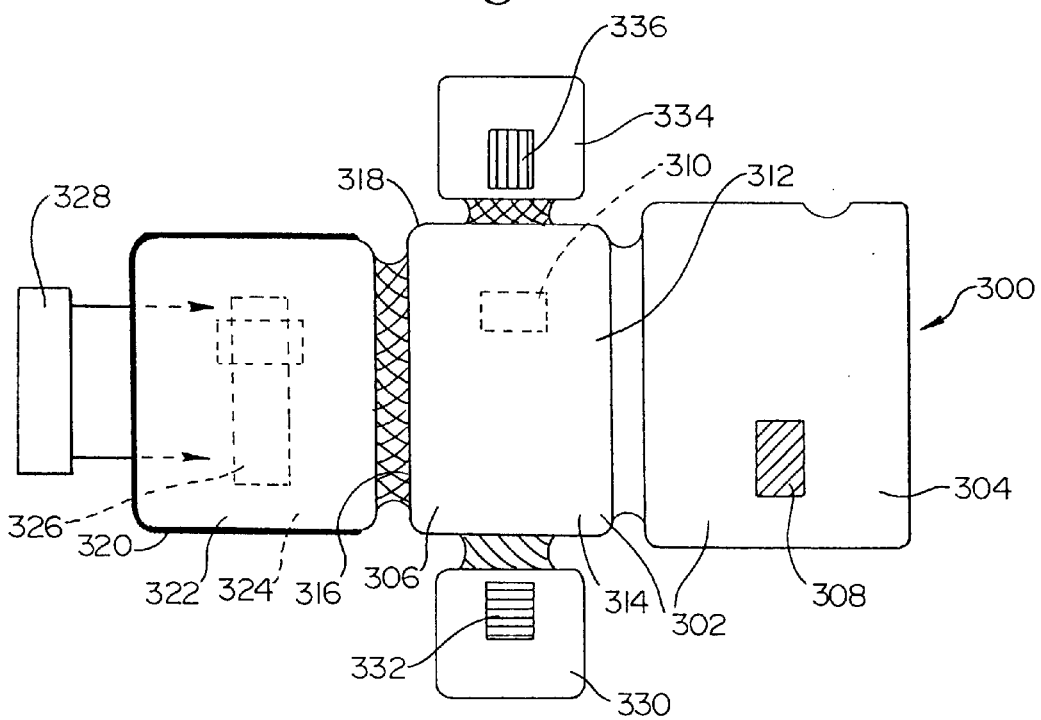
FIG. 7 is a drawing of a seventh embodiment of an assay device according to the present invention with a plurality of hinged reaction panels, removably attachable modules, and a receptacle for a test strip.

Another embodiment of the present invention employs both the multiplicity of removably hinged panels of FIG. 5 and the insertable test strip of FIG. 6. This embodiment of the assay device is depicted in FIG. 7.

The assay device 300 has a first module 302 including a first support panel 304 and a second support panel 306. The first support panel 304 includes thereon a sample preparation zone 308. The second support panel has an aperture 310 and has first, second, third, and fourth sides 312, 314, 316, and 318 as described above. The second support panel 306 is hingedly attached to the first support panel 304 via the first side 312 of the second support panel 306. The device further comprises a second module 320 comprising a third support panel, the third support panel having first and second surfaces 322 and 324 and having a receptacle 326 for a test strip 328. The receptacle 326 is positioned such that when the test strip 328 is inserted into the receptacle 326, the surface of the test strip is accessible from the second surface 324 of the third support panel. The second module 320 is removably hingedly attachable to the third side 316 of the second support panel 306 of the first module 302. The device further comprises a third module 330 that is a first reaction panel that has a first reaction pad 332 thereon. The third module 330 is removably hingedly attachable to the second side 314 of the second support panel 306 of the first module 302. The device further comprises a fourth module 334 that is a second reaction panel that has a second reaction pad 336 thereon. The fourth module 330 is removably hingedly attachable to the fourth side 318 of the second support panel 306 of the first module 302. The operation of this device is substantially equivalent to that of the device shown in FIG. 5, except that, as for the device shown in FIG. 6, a test strip is inserted into the receptacle during the performance of the assay.

H. Device with Slidably Movable Test Strip

Another embodiment of an assay device according to the present invention employs a slidably movable test strip mounted on the device. In this device, the test strip slides between a first position in operable contact with a receptacle for a sample collection device and a second position in which the test strip is not in operable contact with the receptacle for the sample collection device.

Figure 8:
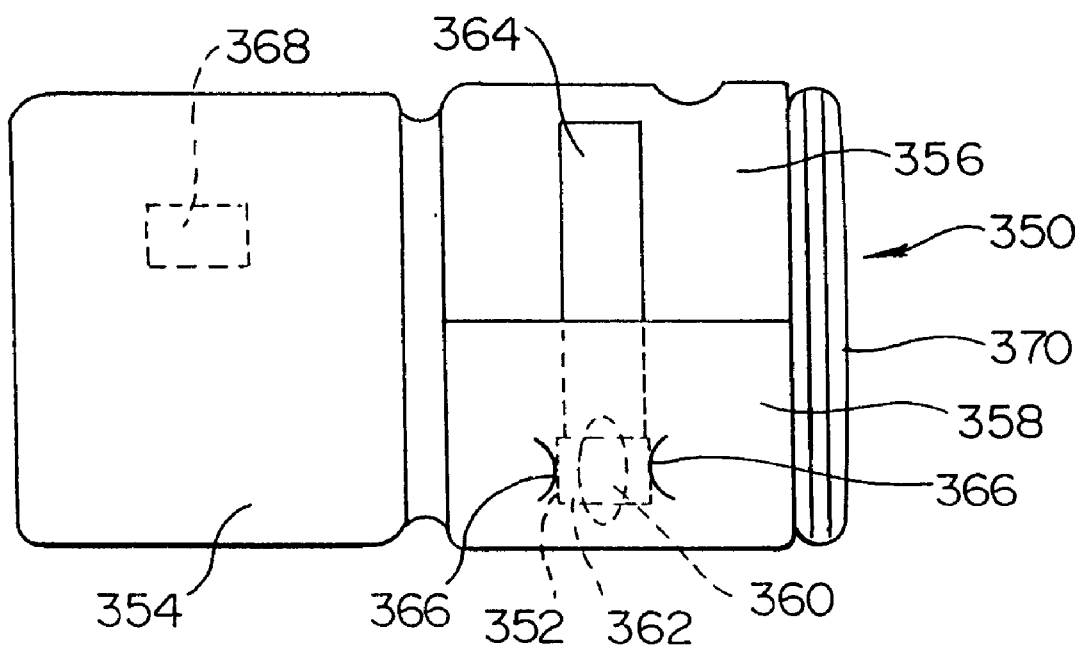
FIG. 8 is a drawing of an eighth embodiment of an assay device according to the present invention with a slidably movable test strip.

This device is shown in FIG. 8. The device 350 has a first opposable component 352 and a second opposable component 354 hingedly attached to the first opposable component 352. The first opposable component 352 includes a first panel 356 and a second panel 358. The second panel 358 is mounted on the first panel 356 generally parallel to the first panel 356 with space between the first and second panels 356 and 358. The second panel 358 has an opening forming a first receptacle 360 for a sample collection device. A second receptacle 362 for a test strip 364 is formed by the first panel 356 and the second panel 358. The test strip 364 is placed in the second receptacle 362 and forms part of the device 350. The second receptacle 362 has slidable contact means 366 to hold the test strip 364 slidably in one of two positions: a first position in which the test strip 364 is in operable contact with a sample collection device placed in the first receptacle 360, and a second position in which the test strip 364 is not in operable contact with a sample collection device placed in the first receptacle 360.

The second opposable component 354 typically has an aperture 368 for viewing of at least a portion of the test strip 364. The first and second opposable components 352 and 354 are also preferably joined by engaging means such as a lock 370 to hold the first and second opposable components 352 and 354 together in proper relation for performance of the assay.

In use, the device 350 is supplied with the test strip 364 in its first position. The test strip 364 is then moved to its second position and a sample collection device such as a swab is placed in the first receptacle 360. Sample extraction or other manipulations are performed, and the test strip 364 is then moved back to its first position and the device 350 closed by bringing the first and second opposable components 352 and 354 into opposition. This initiates performance of the assay.

II. TEST KITS

Another aspect of the present invention is test kits for the performance of assays using the devices of the present invention. The use of insertable test strips and removably hingedly attachable components provide great flexibility in the assembly of test kits.

One example of a test kit according to the present invention comprises, in separately packaged containers:
(1) the assay device of FIG. 1; and
(2) a test strip backed with adhesive and a releasable liner for insertion into the second receptacle of the assay device.

This test kit can further comprise, separately packaged, at least one additional reagent for application either to the sample collection device or the test strip. The additional reagent can form an extraction reagent when applied to the sample collection device; a typical extraction reagent formed is nitrous acid.

Similarly, another test kit according to the present invention can comprise:
(1) the assay device of FIG. 2; and
(2) a test strip backed with adhesive and a releasable liner as described above.

This test kit can further comprise at least one additional reagent as described above.

Another test kit according to the present invention comprises, packaged in separate containers:
(1) the test device of FIG. 3; and
(2) a test strip backed with adhesive and a releasable liner as described above.

This test kit can further comprise at least one additional reagent as described above as well.

However, because the test device of FIG. 3 has two separable modules, an alternative test kit employing this device can comprise:
(1) the first module of the assay device of FIG. 3;
(2) the second module of the assay device of FIG. 3; and
(3) a test strip backed with adhesive and a releasable liner as described above. Additional reagents can also be used.

Alternatively, the test kit can comprise at least two second modules of the assay device so that alternate tests can be performed, for example, for two different bacterial or viral antigens. In this alternative, at least two test strips are provided, one for each second module. Each test strip is backed with adhesive and a releasable liner.

Another embodiment of test kits according to the present invention comprises, in separately packaged containers:
(1) the assay device of FIG. 5; and
(2) at least one reagent to be added to any of the sample preparation zone, the first reaction pad, or the second reaction pad as required to perform the assay. This reagent can be a substrate for an enzyme, a labeled specific binding partner for an analyte, a wash liquid, or another reagent.

Another test kit according to the present invention can comprise:
(1) the assay device of FIG. 6; and
(2) a test strip backed with adhesive and a releasable liner as described above. Additional reagents can also be included.

Another test kit according to the present invention can comprise:
(1) the assay device of FIG. 7; and
(2) a test strip backed with adhesive and a releasable liner.

Alternatively, the assay device of FIG. 7 can be packaged in its individual modules so that the first, second, third, and fourth modules can be packaged separately. In this arrangement multiple third or fourth modules can be furnished to allow the performance of different types of assays, perhaps involving different enzymes or other labels. As with other test kits according to the present invention, at least one additional reagent can also be included.

Another embodiment of a test kit according to the present invention can comprise:
(1) the assay device of FIG. 8; and
(2) at least one additional reagent for application either to the sample collection device or the test strip.

Other reagents that are provided as part of test kits are packaged separately and can be in liquid or solid form (freeze-dried, crystallized, precipitated, or aggregated). If the latter, they are resolubilized by the user, typically with distilled or purified water, physiological saline, or a buffer solution. Other aqueous solvents can also be used.

III. ANALYTES AND ANTIBODIES FOR USE WITH ASSAY DEVICES

The analytes suitable for detection with an assay device according to the present invention include antigens, haptens, and antibodies. Antigens detectable with an assay device according to the present invention include hemoglobin, Streptococcus A and B antigens, antigens specific for the protozoan parasite Giardia, and viral antigens, including antigens specific for HIV and the Australia antigen specific for hepatitis. Antibodies that can be assayed include antibodies to bacteria such as *Helicobacter pylori* and viruses, including HIV. Haptens detectable include any haptens to which antibodies of sufficient specificity can be prepared.

If the analyte is an antigen or a hapten and a sandwich procedure is used, the first and second specific binding partners are preferably antibodies. In many applications, it is preferable that the first and second specific binding partners are antibodies to different epitopes on the analyte, but this is not required. The antibodies can be polyclonal or monoclonal, and can be IgG, IgM, or IgA. In many applications, polyclonal antibodies are preferred, as their natural variability may allow more accurate detection in systems in which antigenic polymorphisms exist or may exist.

When the analyte is a hapten and a sandwich assay procedure is used, it is strongly preferred that the first and second specific binding partners be antibodies binding different epitopes; otherwise, there may be an undesirable competition reaction set up that may interfere with binding of the complex of the labeled specific binding partner and the analyte to the immobilized second specific binding partner. It is recognized that not all haptens are large enough to accommodate more than one epitope; however, some haptens that are not large enough to induce antibody formation when injected by themselves, are nevertheless large enough that they possess more than one epitope. In cases where antibodies to more than one epitope of a hapten cannot be obtained, competitive assay procedures are generally preferred.

Where the analyte is an antibody and a sandwich assay procedure is used, the first specific binding partner is typically a labeled antibody that binds the analyte on the basis of species, class, or subclass (isotype) specificity. It is highly preferred that the first specific binding partner to an antibody analyte bind to the constant region of the antibody analyte, in order to prevent interference. When the analyte is an antibody, the second specific binding partner is preferably an antigen or hapten for which the antibody analyte is specific.

In some applications, it is desirable to employ indirect labeling. For example, in testing for Giardia antigen, an IgM antibody can be used that may be difficult to label directly. In that case, a secondary specific binding partner specific for the mobile first specific binding partner can be labeled. Typically, the labeled secondary specific binding partner binds to the antibody that is the first specific binding partner on the basis of species, class, or subclass specificity. As an alternative to the use of a secondary specific binding partner, the first specific binding partner can be conjugated to biotin and an avidin-conjugated label can be used.

Although assay devices according to the present invention typically perform sandwich immunoassays, such devices can also perform competitive immunoassays. Various combinations of labeled and unlabeled specific binding partners and analyte analogues are known in the art and can be used.

EXAMPLE

The invention is illustrated by the following Example. The Example is for illustrative purposes only and is not to be construed as limiting the scope of the invention in any manner.

A test for Group A streptococci is run using the device of FIG. 1. A swab containing Group A streptococci is placed into the first receptacle. Nitrous acid, or another suitable extraction reagent, is added to the swab in the first receptacle. Such a reagent serves as a carrier, and, if necessary, a means of treating the specimen thereby releasing or exposing the analyte to be detected. Also, a labeled specific binding partner to the analyte is added, such as gold-labeled anti-Group A streptococcal antibody. Alternatively, the labeled specific binding partner can be present on the test strip in resolubilizable form.

The first and second opposable components are closed and sealed along their margins by the closure. This action serves two functions. First, the sample delivery system is positioned properly to receive the test strip assembly. Second, closure of the housing provides containment of the specimen which minimizes the risk of exposure to potentially pathogenic agents.

A test strip assembly is then inserted into the device after the backing is removed from the test strip. The components are keyed in such a manner that the test strip assembly can only be inserted into the housing in the proper orientation. When inserted, the test strip assembly contacts the swab and fluid migration occurs. The result of the test is then read after the appropriate incubation period, typically 5 minutes, through the aperture. If Group A streptococci are present in the sample, a colored band or zone appears in the aperture.

ADVANTAGES OF THE INVENTION

Chromatographic assay devices according to the present invention provide an advantage in being constructed of opposable elements. The use of opposable elements provides great versatility, as it permits the performance of reactions in a number of different sequences. This is possible because the use of such opposable elements allows the delivery of reagents to precisely defined regions of a test strip or other reaction component. The use of opposable elements also provides optimum performance with minimum consumption of reagents by ensuring that reagents are not wasted by being sequestered in dead volumes of apparatus. Finally, the use of opposable components provides optimum containment of possibly contaminated blood samples, such as those containing HIV or hepatitis virus.

Additionally, chromatographic assay devices according to the present invention, as well as other assay devices not employing chromatography, allow the rapid and accurate detection of clinically important antigens, such as Streptococcus A and B antigen, hemoglobin for the determination of fecal occult blood, and antibody to *Helicobacter pylori,* as well as many other antigens. The construction of the devices allows more even application of samples and reagents to the chromatographic medium or other test strip, and reduces interference that might otherwise be introduced by particulates or colored samples.

Extraction of biological samples such as blood, sputum, or feces can be performed directly in the devices, reducing the quantity of contaminated material that must be disposed and reducing the likelihood of accidental infection of physicians, technicians, or the public by such contaminated material. Additionally, the devices are capable of performing bidirectional chromatography to further increase accuracy and reduce interference. Test methods using devices according to the present invention have a wide dynamic range and are substantially free from false negatives that may occur in other test methods at high concentrations of analyte.

The assay devices of the present invention also provide savings in manufacturing costs and time, particularly in packaging, because of their construction. Only the biologically active components need be sealed in a low humidity environment. The housings need not be moisture-free, and the steps needed to ensure that the housings would be moisture-free can be eliminated. This saves on equipment and production costs. The elimination of moisture-free packaging for the housings also reduces the volume of packaging material required and saves on storage and shipment.

Additionally, the use of a separate test strip assembly or chromatographic medium allows for further flexibility in the performance of the immunochromatographic or other test. For example, the housing and its attached sample delivery system can be placed into a heating device. Because the test strip assembly is not a fixed component, more stringent conditions can be employed to treat a sample, such as the use of heat extraction, if the test procedure warrants. Additionally, the separate test strip, once developed, can be removed from the device for insertion into a reading device, such as a spectrophotometer or fluorimeter, for quantitation of the result.

Although the present invention has been described with considerable detail, with reference to certain preferred versions thereof, other versions and embodiments are possible. These versions include other arrangements of two- or three-component devices that operate by the basic principles described herein. These versions include assay devices adapted for performance of competitive immunoassays as well as sandwich immunoassays, in various arrangements, as well as assays other than immunoassays. In particular, devices according to the present invention can be adapted to make use of radial or circumferential flow through a chromatographic medium or other test strip rather than linear flow.

Therefore, the scope of the invention is determined by the following claims.

We claim:

1. An assay device for use with an insertable test strip for detection or determination of an analyte in a liquid sample, comprising:
   (a) a first opposable component comprising:
      (i) a first panel;
      (ii) a second panel mounted on the first panel parallel to the first panel, the second panel comprising an opening forming a first receptacle for holding a sample collection device; and
      (iii) a second receptacle for insertion of the test strip formed by the first panel and the second panel, the insertion occurring during performance of an assay; and
   (b) a second opposable component hingedly attached to the first opposable component;
   wherein the first and second opposable components are pressed together into operable contact to express fluid from the sample collection device to the inserted test strip thereby applying the sample to the test strip, the test strip comprising at least one assay reagent which reacts with the analyte to produce a detectable signal which indicates the presence or amount of the analyte in the sample.

2. The assay device of claim 1 wherein the test strip comprises a chromatographic medium comprising a first end and a second end such that when the test strip is inserted into the second receptacle and when the first and second opposable components are brought into said operable contact, the fluid expressed from the sample collection device is applied to the first end of the chromatographic medium.

3. The assay device of claim 1 wherein the second opposable component further comprises an aperture for view of at least a portion of the test strip.

4. A test kit comprising, in separately packaged containers:
   (a) the assay device of claim 1; and
   (b) at least one sample pretreatment or a second assay reagent for application either to the sample collection device or the test strip, respectively.

5. The test kit of claim 4 further comprising said sample collection device, wherein the sample collection device is impregnated with a second sample pretreatment reagent which reacts with said at least one sample pretreatment reagent to form an extraction reagent which extracts the analyte from the sample when the sample is applied to the sample collection device and contacted with the at least one sample pretreatment reagent.

6. The test kit of claim 5 wherein the extraction reagent formed is nitrous acid.

7. The assay for the detection or determination of said analyte comprising the steps of:
   (a) providing the assay device of claim 1, the sample collection device and the test strip, wherein the test strip is covered wit a releasable liner by means of an adhesive layer,
   (b) collecting the sample on the sample collection device;
   (c) inserting the sample collection device with the sample into the first receptacle of the assay device of claim 1;
   (d) removing the releasable liner from the test strip of step (a) and inserting the test strip from which the releasable liner has been removed into the second receptacle of the assay device of claim 1;
   (e) pressing the first and second opposable components into said operable contact to express the fluid from the sample collection device to apply the sample to the test strip; and
   (f) observing or measuring the presence or amount of the detectable signal produced on the test strip in response to the sample applied to it in order to detect or determine the analyte in the sample.

8. The assay of claim 7 further comprising the step of applying at least one sample pretreatment or a second assay reagent to the sample collection device prior to collecting the sample.

9. A test kit comprising, in separately packaged containers:
   (a) the assay device of claim 1; and
   (b) the test strip for insertion into the second receptacle of the assay device, the test strip being covered with a releasable liner by means of an adhesive layer.

10. An assay device for use with an insertable test strip for detection or determination of an analyte in a liquid sample, comprising:
    (a) a first opposable component comprising:
       (i) a first panel;
       (ii) a second panel mounted on the first panel parallel to the first panel, the second panel comprising an opening forming a first receptacle for holding a swab; and
       (iii) a second receptacle for insertion of the test strip formed by the first panel and the second panel, the insertion occurring during performance of an assay; and
    (b) a second opposable component hingedly attached to the first opposable component;
    wherein the first and second opposable components are pressed together into operable contact to express fluid from the swab to the inserted test strip thereby applying the sample to the test strip, the test strip comprising at least one assay reagent which reacts with the analyte to produce a detectable signal which indicates the presence or amount of the analyte in the sample.

11. An assay device for use with an insertable test strip for detection or determination of an analyte in a liquid sample, comprising:
    (a) a first opposable component comprising:
       (i) a first panel;
       (ii) a second panel mounted on the first panel parallel to the first panel, the second panel comprising an opening forming a first receptacle for holding a sample collection device; and
       (iii) a second receptacle for insertion of the test strip formed by the first panel and the second panel, the insertion occurring during performance of an assay; and (b) a second opposable component hingedly attached to the first opposable component;
    wherein the first and second opposable components are pressed together into operable contact to express fluid from the sample collection device to the inserted test strip thereby applying the sample to the test strip, the test strip comprising at least one assay reagent which reacts with the analyte to produce a detectable signal which indicates the presence or amount of the analyte in the sample, wherein the test strip comprises a chromatographic medium comprising a first end and a second end such that when the test strip is inserted into the second receptacle and when the first and second opposable components are brought into said operable contact, the fluid expressed from the sample collection device is applied to the first end of the chromatographic medium, wherein the chromatographic medium further comprises a detection zone comprising an immobilized specific binding partner for the analyte and wherein the second opposable component further comprises an aperture for viewing of the detection zone.

12. An assay device for use with an insertable test strip for detection or determination of an analyte in a liquid sample, comprising:
   (a) a first opposable component comprising:
      (i) a first panel; and
      (ii) an opening forming a first receptacle for holding a sample collection device in the first panel;
   (b) a second opposable component hingly attached to the first panel of the first opposable component, the second opposable component comprising an aperture; and
   (c) a third opposable component hingedly attached to the second opposable component, the third opposable component comprising a second receptacle for insertion of the test strip, the insertion occurring during performance of an assay;
   wherein the second and third opposable component are foldable and the first and second opposable components are pressed together into operable contact when the second opposable component has been folded over the third opposable component to express fluid through said aperture from the sample collection device to the inserted test strip thereby applying the sample to the test strip, the test strip comprising at least one assay reagent which reacts with the analyte to produce a detectable signal which indicates the presence or amount of the analyte in the sample.

13. The assay device of claim 12 wherein the first receptacle is shaped to hold a swab.

14. The assay device of claim 12 wherein the test strip comprises a chromatographic medium comprising a first end and a second end such that when the test strip is inserted into the second receptacle and the first and second opposable components are brought into said operable contact, the fluid expressed from the sample collection device is applied to the first end of the chromatographic medium.

15. The assay device of claim 14 wherein the chromatographic medium further comprises a detection zone comprising an immobilized specific binding partner for the analyte and the detection zone is visible through the aperture.

16. A test kit comprising, in separately packaged containers:
   (a) the assay device of claim 12; and
   (b) at least one sample pretreatment or a second assay reagent for application either to the sample collection device or the test strip, respectively.

17. The test kit of claim 16 further comprising said sample collection device, wherein the sample collection device is impregnated with a second sample pretreatment reagent which reacts with said at least one sample pretreatment reagent to form an extraction reagent which extracts the analyte from the sample when the sample is applied to the sample collection device and contacted with the at least one sample pretreatment reagent.

18. The test kit of claim 17 wherein the extraction reagent formed is nitrous acid.

19. The assay for the detection or determination of said analyte comprising the steps of:
   (a) providing the assay device of claim 12, the sample collection device, and a test strip, wherein the test strip is covered with a releasable liner by means of an adhesive layer;
   (b) collecting the sample on the sample collection device;
   (c) inserting the sample collection device with the sample into the first receptacle of the assay device of claim 12;
   (d) removing the releasable liner from the test strip of step (a) and inserting the test strip from which the releasable liner has been removed into the second receptacle of the assay device of claim 12;
   (e) folding the third opposable component over the second opposable component;
   (f) folding the second and third opposable components together over the first opposable component and pressing the sample collection device into said operable contact with the test strip to express the fluid sample the sample collection device to apply the sample to the test strip; and
   (g) observing or measuring the presence or amount of the detectable signal produced on the test strip in response to the sample applied to it in order to detect or determine the analyte in the sample.

20. The assay of claim 19 further comprising the step of applying at least one sample pretreatment or a second assay reagent to the sample collection device after inserting the sample collection device into the first receptacle.

21. A test kit comprising, in separately packaged containers:
   (a) the assay device of claim 12; and
   (b) the test strip for insertion into the second receptacle of the assay device, the test strip being covered with a releasable liner by means of an adhesive layer.

22. An assay device for use with an insertable test strip for detection or determination of an analyte in a liquid sample, comprising:
   (a) a first module comprising:
      (i) a first panel, the first panel comprising a receptacle for holding a sample collection device;
      (ii) a second panel hingedly attached to the first panel, the second panel comprising an aperture for viewing of a portion of the test strip; and
   (b) a second module comprising a second receptacle for insertion of the test strip, the insertion occurring during performance of an assay, the second module reversibly hingedly attachable to the second panel of the first module;
   wherein, when the second module is attached to the first module, the second module is folded over the second panel of the first module, and the second module and or second panel of the first module are then folded together over the first panel of the first module to press to the second module and the first panel of the first module into operable contact to express fluid from the sample collection device thereby applying the sample to the test strip, the test strip comprising at least one assay reagent which reacts with the analyte to produce a detectable signal which indicates the presence or amount of the analyte in the sample.

23. The assay device of claim 22 wherein the first receptacle is shaped to hold a swab.

24. The assay device of claim 22 wherein the test strip comprises a chromatographic medium comprising a first end and a second end such that when the test strip is inserted into the second receptacle and the first and second components are brought into said operable contact, the fluid expressed from the sample collection device is applied to the first end of the chromatographic medium.

25. The assay device of claim 24 wherein the chromatographic medium comprises a detection zone comprising an immobilized specific binding partner for the analyte and wherein the aperture of the second portion of the first module allows viewing of the detection zone when the second module is folded over the second panel of the first module.

26. A test kit comprising, in separately packaged containers:
   (a) the assay device of claim 22; and
   (b) at least one sample pretreatment or a second assay reagent for application either to the sample collection device or the test strip, respectively.

27. The test kit of claim 26 further comprising said sample collection device, wherein the sample collection device impregnated with a second sample pretreatment reagent which reacts with said at least one sample pretreatment reagent to form an extraction reagent which extracts the analyte from the sample when the sample is applied to the sample collection device and contacted with the at least one sample pretreatment reagent.

28. The assay for the detection or determination of said analyte comprising the steps of:
   (a) providing the assay device of claim 22, the sample collection device and the test strip, wherein the test strip is covered with a releasable liner by means of an adhesive layer, (b) collecting tie sample on the sample collection device;
   (c) inserting the sample collection device with the sample into the first receptacle of the first panel of the first module of the assay device of claim 22;
   (d) removing the releasable liner from the test strip of step (a) and insert the test strip from which the releasable liner has been removed into the second receptacle of the second module of the assay device of claim 22;
   (e) attaching the second module of the assay device with inserted test strip to the second panel of the first module of the assay device;
   (f) folding the second module of the assay device over the second panel of the first module of the assay device;
   (g) folding the second module and the second panel of the first module of the assay device together over the first panel of the first module of the assay device to place the test strip into said operable contact with the sample collection device to express the fluid from the sample collection device to apply the sample to the test strip; and
   (h) observing or measure the presence or amount of the detectable signal produced on the test strip in response to the sample applied to it in order to detect or determine the analyte in the sample.

29. A test kit comprising, in separately packaged containers:
   (a) the assay device of claim 22; and
   (b) the test strip for insertion into the second receptacle of the assay device, the test strip being covered with a releasable liner by means of an adhesive layer.

30. An assay device for detection or determination of an analyte in a liquid sample comprising:
   (a) a first support panel comprising a sample application zone;
   (b) a second support panel hingedly attached to the first support panel and comprising an aperture for viewing a test strip, the second support panel comprising fist, second, third and fourth sides with the first and third sides being parallel and the second and fourth sides being parallel, with the first side being hingedly attached to the first support panel,
   (c) a third support panel hingedly attached to the third side of the second support panel, the third support panel comprising first and second surfaces with the test strip attached to the second surface, the test strip comprising an immobilized specific binding partner for the analyte;
   (d) a first reaction panel hingedly attached to the second side of the second support panel comprising a first reaction pad comprising a resolubilizable first reagent to be applied to a first portion of the test strip, wherein the first reagent is (i) an extraction reagent for releasing the analyte for the sample of (ii) a specific binding partner for the analyte or the analyte, coupled to a label which produces a detectable signal which indicates the presence or amount of the analyte in the sample;
   (e) a second reaction panel hingedly attached to the fourth side of the second support panel comprising a second reaction pad comprising a resolubilizable second reagent to be applied to a second portion of the test strip upstream from the first portion, wherein the second reagent is (i) the labeled specific binding partner for the analyte or the labeled analyte, (ii) a reagent which reacts with the label to produce or amplify the detectable signal or (iii) a buffer or salt;
   wherein the third support panel is folded over the second support panel and the combination of the second and third support panels is then folded over the first support panel such that the test strip is in operable contact with the sample application zone, and wherein, when the third support panel is folded over the second support panel, the first reaction panel is in operable contact with the first portion of the test strip, and when the second reaction panel is folded over the third support panel, the second reaction pad is in operable contact with the second portion of the test strip.

31. The assay device of claim 30 wherein the test strip comprises a chromatographic medium.

32. The assay device of claim 31 wherein the chromatographic medium comprises first and second ends, the first end comprising the first portion of the test strip and the second end comprising the second portion of the test strip.

33. The assay device of claim 30 wherein the first reagent is said extraction reagent.

34. The assay device of claim 30 wherein the first reagent is said labeled specific binding partner.

35. The assay device of claim 30 wherein the second reagent is said labeled specific binding partner.

36. The assay device of claim 30 wherein the first reagent is an enzyme-labeled specific binding partner for the analyte;
   and the second reagent is a substrate which reacts with the enzyme label to produce said detectable signal.

37. The assay device of claim 36 wherein the enzyme label is selected from the group consisting of horseradish peroxidase, β-galactosidase, glucose oxidase, and alkaline phosphatase.

38. The assay device of claim 30 wherein the first reagent is said labeled specific binding partner and the second reagent is a amplifying reagent.

39. The assay device of claim 38 wherein the labeled specific binding partner is labeled with a gold sol label and the amplifying reagent comprises a quinone and a soluble silver salt.

40. The assay for detecting or determining said analyte in said sample comprising the steps of:
   (a) applying the sample to the sample application zone of the assay device of claim 30;

(b) folding the third support panel over the second support panel of the assay device of claim 30 and then folding the combined third and second support panels over the first support panel, pressing the sample application zone into said operable contact with the test strip to apply the sample to the test strip;

(c) unfolding the second and third support panels from the first support panel and refolding the third support panel over the second suppor panel;

(d) folding the first and second reaction panels over the second support panel, pressing the first and second reaction pads into said operable contact with the test strip to resolubilize and apply the first and second reagents to the test strip;

(e) allowing the sample and thc first and second reagents to migrate through at least said first and second portions of the test strip; and (f) detecting or determining the analyte by observing or measuring the presence or amount of the detectable signal produced by the label specifically bound to said immobilized specific binding partner.

41. An assay device for detection or determination of an analyte in a liquid sample comprising:

(a) a first module comprising:
 (i) a first support panel comprising a sample application zone; and
 (ii) a second support panel comprising an aperture therein for viewing a test strip and comprising first, second, third and fourth sides with the first and third sides and second and fourth sides being parallel, with the first side of the second support panel being hingedly attached to the first support panel;

(b) a second module comprising a third support panel, the third support panel comprising said test strip, the second module being reversibly hingedly attached to the third side of the second support panel of the first module, the test strip comprising an immobilized specific binding partner for the analyte;

(c) a third module comprising a first reaction panel comprising a first reaction pad, said first reaction panel reversibly hingedly attached to the second side of the second support panel of the first module, the first reaction pad comprising a resolubilizable first reagent to be applied to first portion of the test strip wherein the first reagent is (i) an extraction reagent for releasing the analyte from the sample or (ii) a specific binding partner for the analyte or the analyte, coupled to a label which produces a detectable signal which indicates the presence or amount of the analyte in the sample; and (d) a fourth module comprising a second reaction panel comprising a second reaction pad, said second reaction panel reversibly hingedly attached to the fourth side of the second support panel of the first module, the second reaction pad comprising a resolubilizable second reagent to be applied to a second portion test strip upstream of the first portion, wherein the second reagent is (i) the labeled specific binding partner for the analyte or the labeled analyte; (ii) a reagent which reacts with the label to produce or amplify the detectable signal or (iii) a buffer or salt;

wherein the second module is folded over the second support panel of the first module, and the second module and the second support panel of the first module are then folded over the first support panel of the first module the sample application zone is pressed into operable contact with the test strip; and when the second module is folded over the second support panel of the first module, and the third module is folded over the second support panel of the first module and the second module to press the first reaction pad into said operable contact with the first portion of the test strip to apply the first reagent to the test strip and the fourth module is folded over the second support panel of the first module and the second module to press the second reaction pad into said operable contact with the second portion of the test strip to apply the second reagent to the test strip.

42. The assay device of claim 41 wherein the test strip comprises a chromatographic medium.

43. The assay device of claim 42 wherein the chromatographic medium comprises a first end and second end, the first end comprising the first portion of the test strip and the second end comprising the second portion of the test strip, and the sample application zone is in operable contact with the first end of the chromatographic medium when the second module and the second support panel of the first module are folded to over the first support panel of the first module.

44. The assay device of claim 41 wherein the first reagent is said extraction reagent.

45. The assay device of claim 41 wherein the first reagent is said labeled specific binding partner.

46. The assay deice of claim 41 wherein the second reagent is said labeled specific binding partner.

47. The assay device of claim 41 wherein the first reagent is enzyme-labeled specific binding partner, and the second reagent is a substrate which reacts with the enzyme label to produce said detectable signal.

48. The assay device of claim 47 wherein the enzyme label is selected from the group consisting of horseradish peroxidase, β-galactosidase, glucose oxidase, and alkaline phosphatase.

49. The assay device of claim 41 wherein the first reagent is said labeled specific binding partner and the second reagent is said amplifying reagent.

50. The assay device of claim 49 wherein the labeled specific binding partner is labeled with a gold sol label and the amplifying reagent comprises a quinone and a silver salt.

51. A test kit comprising, in separately packaged containers:

(a) the assay device of claim 41; and (b) at least one sample pretreatment reagent for application to any one of either the sample application zone, the first reaction pad, or the second reaction pad, or a second assay reagent for application to any one of either the sample application zone, the first reaction pad, or the second reaction pad.

52. The assay for the detection or determination of said analyte comprising the steps of:

(a) providing the assay device of claim 41;

(b) adding the sample to the sample application zone of the assay device of claim 41;

(c) folding the second module of the assay device over the second support panel of the first module and then folding the combined second module and the second support panel of the first module over the first support panel of the first module, pressing the test strip into operable contact with the sample application zone;

(d) unfolding the second module and the second support panel of the first module from the first support panel of the first module and then folding the third module over the second module, pressing the first reaction pad into said operable contact with the test strip to resolubilize and apply the fist reagent to the test strip and folding the fourth module over the second module, pressing the second reaction pad into said operable contact with the test strip to resolubilize and apply the second reagent to the test strip;

(e) allowing the sample and the first and second reagents to migrate through it least said first and second portions of the test strip; and (f) observing or measuring the presence or amount of the detectable signal produced by the label specifically bound to said immobilized specific binding partner in order to detect or determine the analyte in the sample.

53. An assay device for use with an insertable test strip for detection or determination of an analyte in a liquid sample, comprising:

(a) a first support panel comprising a sample application zone;

(b) a second support panel hingedly attached to the first support panel and comprising an aperture for viewing of the test strip, the second support panel comprising first, second, third and fourth sides with the first and third sides being parallel and the second and fourth sides being parallel, with the first side being hingedly attached to the first support panel;

(c) a third support panel hingedly attached to the third side of the second support panel, the third support panel comprising first and second surfaces and comprising a receptacle for insertion of the test strip such that, when the test strip is inserted into the receptacle, a surface of the test strip is accessible from the second surface of the third support panel;

(d) a first reaction panel hingedly attached to a second side of the second support panel, the first reaction panel comprising a first reaction pad comprising a resolubilizable first reagent to be applied to a first portion of the test strip, wherein the first reagent is (i) an extraction reagent for releasing the analyte from the sample or (ii) a specific binding partner for the analyte or the analyte, coupled to a label which produces a detectable signal which indicates the presence or amount of the analyte in the sample; and (e) a second reaction panel hingedly attached to the fourth side of the second support panel, the second action panel comprising a second reaction pad comprising a resolubilizable second reagent applied to a second portion of the test strip upstream from the first portion wherein the second reagent is (i) the labeled specific binding partner for the analyte or the labeled analyte; (ii) a reagent which reacts with the label to produce or amplify the detectable signal or (iii) a buffer or salt;

wherein the third support panel is folded over the second support panel and the combination of the second and third support panels is then folded over the first support panel, pressing the test strip into operable contact with the sample application zone, and wherein, when the third support panel is folded over the second support panel, the first reaction panel is folded over the third support panel so that the first reaction pad is pressed into operable contact with the first portion of the test strip to apply the first reagent to the test strip and the second reaction panel is folded over the third support panel so that the second reaction is pressed into operable contact with the second portion of the test strip to apply the second reagent to the test strip, the test strip comprising an immobilized specific binding partner for the analyte.

54. The assay device of 53 wherein the test strip comprises a chromatographic medium comprising a first end, and a second end comprising the first portion of the test strip and the second end comprising the second portion of the test strip.

55. The assay device of claim 54 wherein the chromatographic medium comprises a detection zone, the detection zone comprising an immobilized specific binding partner for the analyte, and wherein the aperture is for viewing of the detection zone.

56. The assay device of claim 54 wherein the first reaction pad is in operable contact with the first end of the chromatographic medium, and the second reaction pad is in operable contact with the second end of the chromatographic medium.

57. The assay device of claim 53 wherein the first reagent is said extraction reagent.

58. The assay device of claim 53 wherein the first reagent is said labeled specific binding partner.

59. The assay device of claim 53 wherein the second reagent is said labeled specific binding partner.

60. The assay device of claim 53 wherein the first reagent is an enzyme-labeled specific binding partner for the analyte, and the second reagent is a substrate which reacts with the enzyme label to produce said detectable signal.

61. The assay device of claim 60 wherein the enzyme label is selected from the group consisting of horseradish peroxidase, β-galactosidase, glucose oxidase, and alkaline phosphatase.

62. The assay device of claim 53 wherein the first reagent is said labeled specific binding partner and the second reagent is said amplifying reagent.

63. The assay device of claim 53 wherein the labeled specific binding partner is labeled with a gold sol label and the amplifying reagent comprises a quinone and a soluble silver salt.

64. The assay for the detection or determination of said analyte in a test sample comprising the steps of:

(a) providing the assay device of claim 53 and a test strip, wherein the test strip is covered with a releasable liner by means of an adhesive layer;

(b) applying the sample to the sample application zone of the assay device of claim 53;

(c) removing the releasable liner from the test strip of step (a) and inserting the test strip into the receptacle of the assay device of claim 53;

(d) folding the third support panel over the second support panel and then folding the combined third and second support panels over the first support panel, pressing the sample application zone into said operable contact with the test strip to apply the sample to the test strip;

(e) unfolding the second and third support panels from the first support panel and refolding the third support panel over the second support panel;

(f) folding the first and second reaction panels over the second support panel, pressing the first and second reaction panels into said operable contact with the test strip to resolubilize to apply the first and second reagents to the test strip;

(g) allowing the sample and the first and second reagents to migrate through at least said first and second portions of the test strip; and (h) detecting or determining the analyte by observing or measuring the presence or amount of the detectable signal produced by the label specifically bound to said immobilized specific binding partner.

65. An assay device for use with an insertable test strip for detecting or determining an analyte in a liquid sample, comprising:
(a) a first module comprising:
  (i) a first support panel comprising a sample application zone; and
  (ii) a second support panel comprising an aperture therein for viewing the test strip and comprising first, second, third, and fourth sides with the first and third sides and the second and fourth sides being panel, the second support panel being hingedly attached to the first support panel via the first side of the second support panel;
(b) a second module comprising a third support panel, the third support panel comprising first and second surfaces and comprising a receptacle for insertion of the test strip such that, when the test strip is inserted into the receptacle, a surface of the test strip is accessible from the second surface of the third support panel, the second module being reversibly hingedly attached to the third side of the second support panel of the first module;
(c) a third module comprising a first reaction panel comprising a first reaction pad comprising a resolubilizable first reagent to be applied to a first portion of the test strip, the third module being reversibly hingedly attached to the second side of the second support panel of the first module, wherein the first reagent is (i) an extraction reagent for releasing the analyte from the sample for (ii) a specific binding partner for the analyte or the analyte, coupled to a label which produces a detectable signal which indicates the presence or amount of the analyte in the sample; and
(d) a fourth module comprising a second reaction panel comprising a second reaction pad comprising a second reagent applied to the test strip, the fourth module being reversibly hingedly attached to the second side of the second support panel of the first module, wherein the second reagent is (i) the labeled specific binding partner for the analyte or the labeled analyte; (ii) a reagent which reacts with the label to produce or amplify the detectable signal or (iii) a buffer or salt;
wherein the second module is folded over the second support panel of the first module, the second module and the second support panel of the first module are then folded over the first support panel of the first module such that the sample application zone is pressed into operable contact with the test strip; and when the third module is folded over the second support panel of the first module and the second module, and the fourth module is folded over the second support panel of the first module and the second module such that the first reaction pad is pressed into operable contact with the first portion of the test strip to apply the first reagent to first portion of the test strip and such that the second reaction pad is pressed into operable contact with the second portion of the test strip to apply the second reagent to the second portion of the test strip, the test strip comprising reacts with the analyte to produce a detectable signal which indicates the presence or amount of an immobilized specific binding partner for the analyte.

66. The say device of claim 65 wherein the test strip comprises a chromatographic medium comprising a first end and a second end, the first end comprising the first portion of the test strip and the second end comprising the second portion of the test strip.

67. The assay device of claim 66 wherein the chromatographic medium comprises a detection zone, the detection zone comprising the immobilized specific binding partner for the analyte, and wherein the aperture is for viewing of the detection zone.

68. The assay device of claim 66 wherein the first reaction pad is in operable contact with the first end of the chromatographic medium and the second reaction pad is in operable contact with the second end of the chromatographic medium.

69. The assay device of claim 65 wherein the first reagent is said extraction reagent.

70. The assay device of claim 65 wherein the first reagent is said labeled specific binding partner.

71. The assay device of claim 65 wherein the second reagent is said labeled specific binding partner.

72. The assay device of claim 65 wherein the first reagent is an enzyme-labeled specific binding partner for the analyte, and the second reagent is a substrate which reacts with the enzyme label to produce said detectable signal.

73. The assay device of claim 72 wherein the enzyme label is selected from the group consisting of horseradish peroxidase, β-galactosidase, glucose oxidase, and alkaline phosphatase.

74. The assay device of claim 65 wherein the first reagent is said labeled specific binding partner and the second reagent is said amplifying reagent.

75. The assay device of claim 74 wherein the labeled specific binding partner is labeled with a gold sol label and the amplifying reagent comprises a quinone and a soluble silver salt.

76. The assay for the detection or the determination of said analyte in a test sample comprising the steps of:
(a) providing the assay device of claim 65 and the test strip, wherein the test strip is covered with a releasable liner by means of an adhesive layer;
(b) adding the sample to the sample application zone of the assay device of claim 65;
(c) removing the releasable liner from the test strip of step (a) and inserting the test strip from which the releasable liner has been removed into the receptacle of the assay device of claim 65;
(d) folding the second module of the assay device over the second support panel of the first module and then folding the combined second module and the second support panel of the first module over the first support panel of the first module, pressing the test strip into said operable contact with the sample application zone;
(e) unfolding the second module and the second support panel of the first module from the first support panel of the first module and then folding the third module over the second module, pressing the first reaction pad into said operable contact with the test strip to resolubilize and apply the first reagent to the test strip and folding the fourth module over the second module to press the second reaction pad into said operable contact with the test strip to resolubilize and apply the second reagent to the test strip;
(f) allowing the sample and the first and second reagents to migrate through said first and second portions of the test strip; and
(g) observing or measuring the presence or amount of the detectable signal produced by the label specifically bound to said immobilized specific binding partner to detect or determine the analyte in the sample.

77. An assay device for use with an insertable test strip for detection or determination of an analyte in a sample comprising:

(a) a first opposable component comprising:
  (i) a first panel;
  (ii) a second panel mounted on the first panel parallel to the first panel with space between the first and the second panel, the second panel comprising an opening forming a first receptacle for holding a sample collection device; and
  (iii) a second receptacle for insertion of the test strip formed by the first panel and the second panel, the insertion occurring during performance of an assay, the second receptacle comprising slidable contact means to hold the test strip slidably in one of two positions, a first position in which the test strip is in operable contact with the sample collection device placed in the first receptacle and a second position in which the test strip is not in operable contact with the sample collection device; and
(b) a second opposable component hingedly attached to the first opposable component; wherein the first and second opposable components are pressed together into operable contact to express fluid from the sample collection device to the inserted test strip thereby applying the sample to the test strip for the detection or determination of the analyte, the test strip comprising at least one assay reagent which react with the analyte to produce a detectable signal which indicates the presence or amount of the analyte in the sample.

78. The assay device of claim 77 wherein the first receptacle is shaped to hold a swab.

79. The assay device of claim 77 wherein the test strip comprises a chromatographic medium comprising a first end and a second end such that the test strip is inserted into the second receptacle and when the first and second opposable components are pressed into said operable contact, the fluid expressed from the sample collection device is applied to the first end of the chromatographic medium.

80. The assay device of claim 77 wherein the second opposable component comprises an aperture for viewing of at least a portion of the test strip.

81. The assay device of claim 79 wherein the chromatographic medium comprises a detection zone, the detection zone comprising an immobilized specific binding partner for the analyte, and wherein the second opposable component further comprises an aperture for viewing of the detection zone.

82. A test kit comprising, in separately packaged containers:
  (a) the assay device of claim 77; and
  (b) at least one sample pretreatment or a second assay reagent for application either to the sample collection device or the test strip, respectively.

83. The test kit of claim 82 further comprising said sample collection device, wherein the sample collection device is impregnated with a second sample pretreatment reagent to form an extraction reagent which extracts the analyte from the sample when the sample is applied to the sample collection device and contacted with the at least one sample pretreatment reagent.

84. The test kit of claim 83 wherein the extraction reagent formed is nitrous acid.

85. The assay for the detection or determination of said analyte in a sample comprising the steps of:
  (a) providing the assay device of claim 77, the sample collection device, and the test strip, wherein the test strip is covered with a releasable liner by means of an adhesive layer;
  b) collecting the sample on the sample collection device;
  (c) inserting the test strip of step (a) into the second receptacle of the assay device of claim 77;
  (d) moving the test strip inserted into the second receptacle of the assay device of claim 77 to the second position;
  (e) inserting the sample collection device with the sample into the first receptacle of the assay device of claim 77;
  (f) returning the test strip to the first position;
  (g) pressing the first and second opposable components of the assay device into said operable contact to express the fluid from the sample collection device to apply the sample to the test strip; and
  (h) observing or measuring the presence or amount of the detectable signal produced on the test strip in response to the sample applied to it in order to detect or determine the analyte in the sample.

* * * * *